United States Patent
Marsch et al.

(10) Patent No.: US 12,251,538 B2
(45) Date of Patent: Mar. 18, 2025

(54) AUTOINJECTOR

(71) Applicant: MEDMIX SWITZERLAND AG, Haag (CH)

(72) Inventors: William Geoffrey Arthur Marsch, Stratford-upon-Avon (GB); Anthony Paul Morris, Balsall Common (GB); Matthew Meredith Jones, Warwick (GB); Aled Meredydd James, Solihull (GB)

(73) Assignee: Medmix Switzerland AG, Haag (CH)

( * ) Notice: Subject to any disclaimer, the term of this patent is extended or adjusted under 35 U.S.C. 154(b) by 494 days.

(21) Appl. No.: 17/587,735

(22) Filed: Jan. 28, 2022

(65) Prior Publication Data

US 2023/0125889 A1    Apr. 27, 2023

(30) Foreign Application Priority Data

Oct. 27, 2021    (EP) .................................... 21205074

(51) Int. Cl.
*A61M 5/20* (2006.01)
*A61M 5/315* (2006.01)
*A61M 5/32* (2006.01)

(52) U.S. Cl.
CPC ........ *A61M 5/2033* (2013.01); *A61M 5/3157* (2013.01); *A61M 5/3243* (2013.01);
(Continued)

(58) Field of Classification Search
CPC .............. A61M 5/2033; A61M 5/3157; A61M 5/3243; A61M 2005/2006; A61M 2005/2026; A61M 2005/2086; A61M 2205/581; A61M 2005/2013; A61M 2005/208; A61M 5/20; A61M 2005/202; A61M 5/31566; A61M 5/31571; A61M 2005/2073; A61M 5/31565; A61M 2205/583; A61M 5/326; A61M 2005/206; A61M 2005/3247; A61M 5/3204;
(Continued)

(56) References Cited

U.S. PATENT DOCUMENTS 5,026,349 A    6/1991   Schmitz et al.
8,876,768 B2   11/2014  Hourmand et al.
(Continued)

FOREIGN PATENT DOCUMENTS

EP    2585142 B1    2/2018
EP    2585142 B2 *  2/2018   .............. A61M 5/20
(Continued)

OTHER PUBLICATIONS

U.S. Appl. No. 18/704,861, filed Apr. 35, 2024, Marsh.*
European Search Report issued Apr. 4, 2022 in corresponding European Application No. 21205074.4.

*Primary Examiner* — Michael J Tsai
*Assistant Examiner* — Isabella S North
(74) *Attorney, Agent, or Firm* — Global IP Counselors, LLP

(57) ABSTRACT

An autoinjector includes a housing and a drive chassis arranged linearly moveable within the housing. The drive chassis includes a dispensing limb and a trigger limb. The trigger limb and the dispensing limb are arranged in parallel to one another and are connected to one another at a respective distal end of the dispensing limb and the trigger limb.

15 Claims, 24 Drawing Sheets

(52) U.S. Cl.
CPC ............ *A61M 2005/2006* (2013.01); *A61M 2005/2026* (2013.01); *A61M 2005/2086* (2013.01); *A61M 2205/581* (2013.01)

(58) Field of Classification Search
CPC ........ A61M 5/3202; A61M 2005/3143; A61M 2005/3267; A61M 2207/00; A61M 5/1454; Y10T 74/18984
USPC ........ 604/134, 130, 131, 137, 135, 136, 110
See application file for complete search history.

(56) References Cited

U.S. PATENT DOCUMENTS

| | | |
|---|---|---|
| 9,421,337 B2 | 8/2016 | Kemp et al. |
| 10,561,799 B2 | 2/2020 | Schrul et al. |
| 2015/0202368 A1* | 7/2015 | Carrel ................. A61M 5/2033 604/198 |
| 2020/0171248 A1* | 6/2020 | Mehawej ................ A61M 5/20 604/198 |

FOREIGN PATENT DOCUMENTS

| | | | |
|---|---|---|---|
| WO | WO-2008113199 A1 * | 9/2008 | .......... A61M 5/2033 |
| WO | WO-2020173993 A1 * | 9/2020 | .............. A61M 5/20 |

* cited by examiner

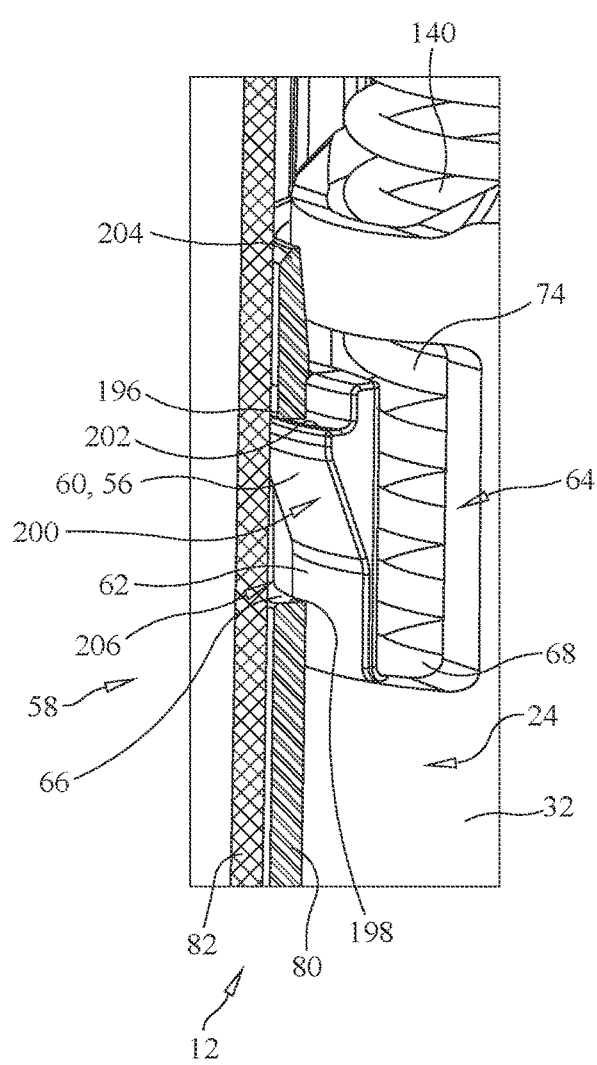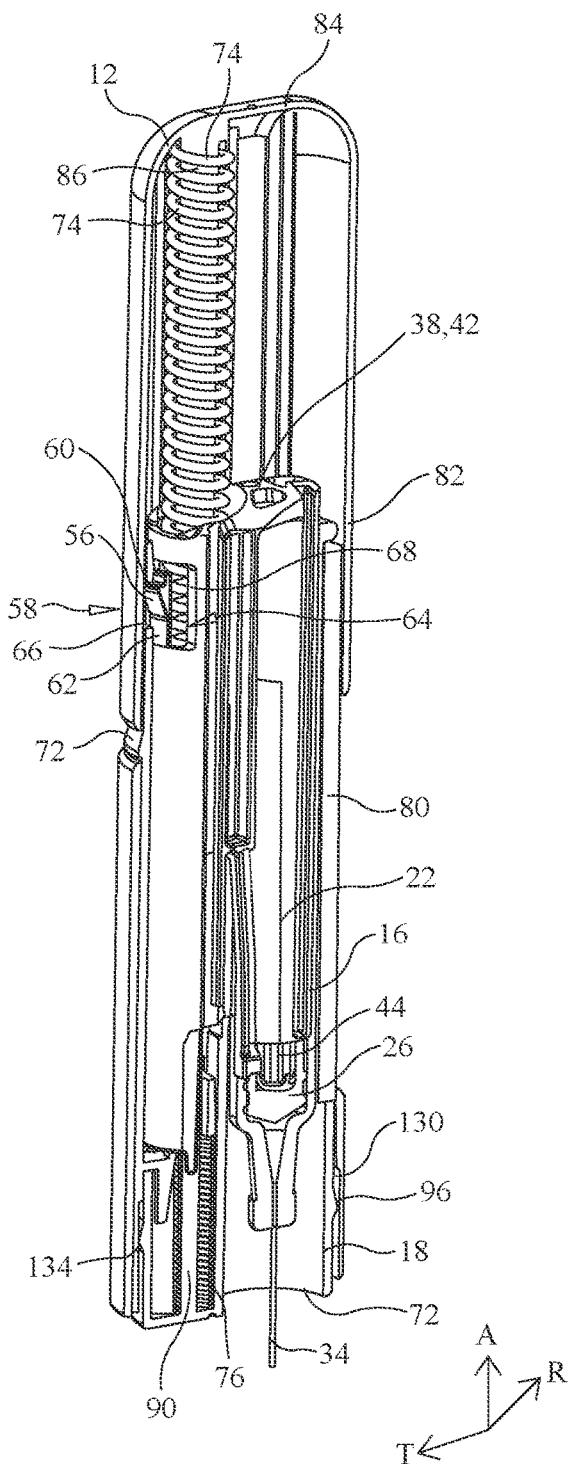
FIG. 11A
FIG. 11B

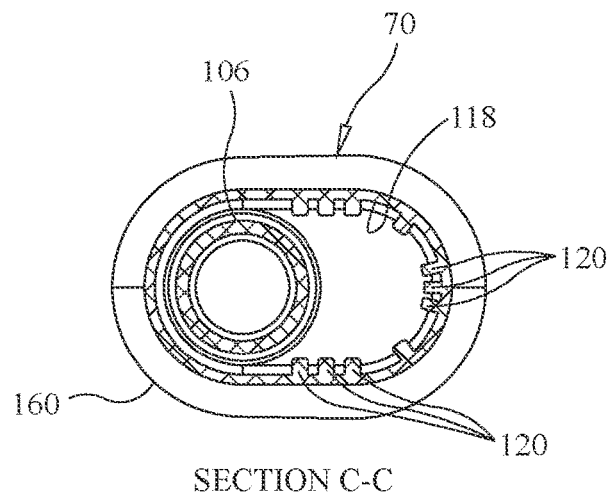
FIG. 12D
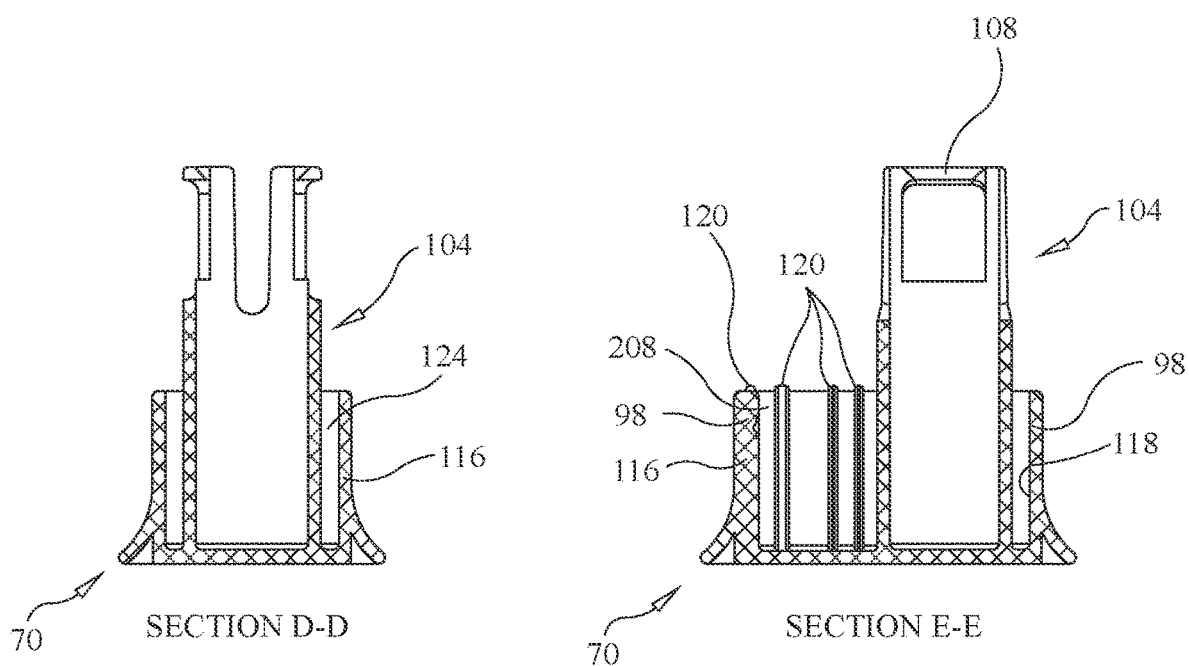
FIG. 12E
FIG. 12F

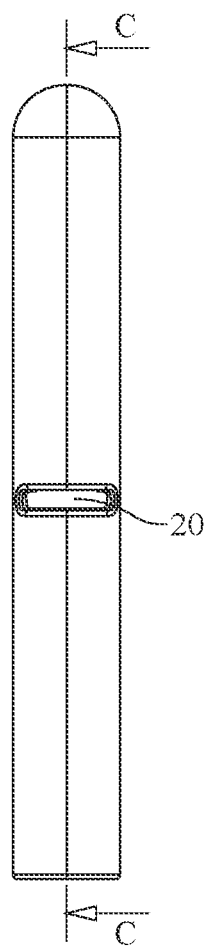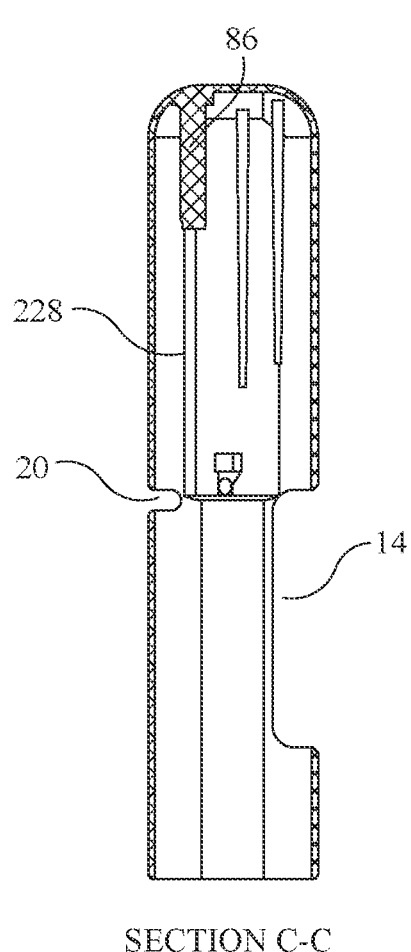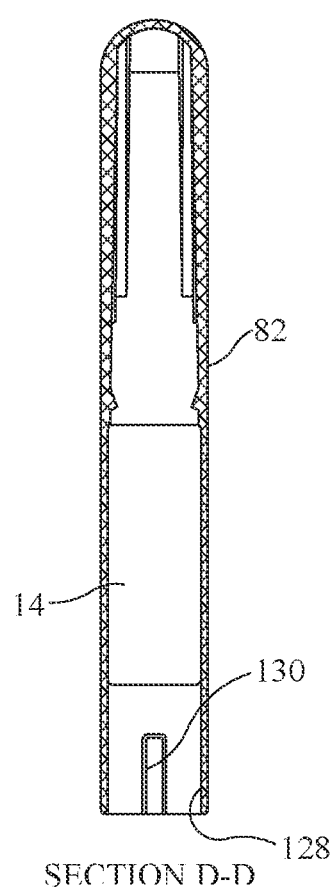
FIG. 13F  FIG. 13G  FIG. 13H
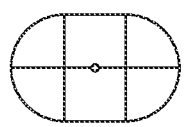
FIG. 13I
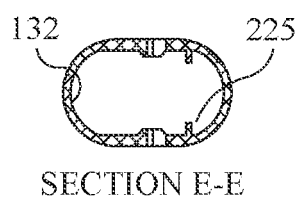
SECTION E-E
FIG. 13J

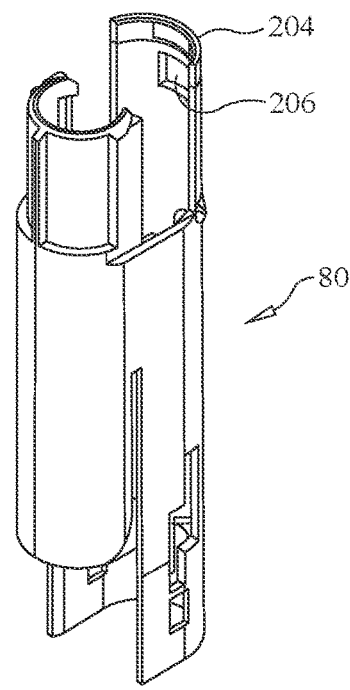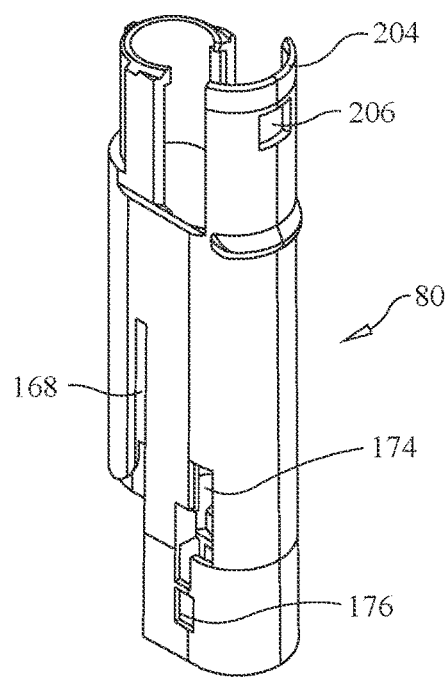
FIG. 14A  FIG. 14B
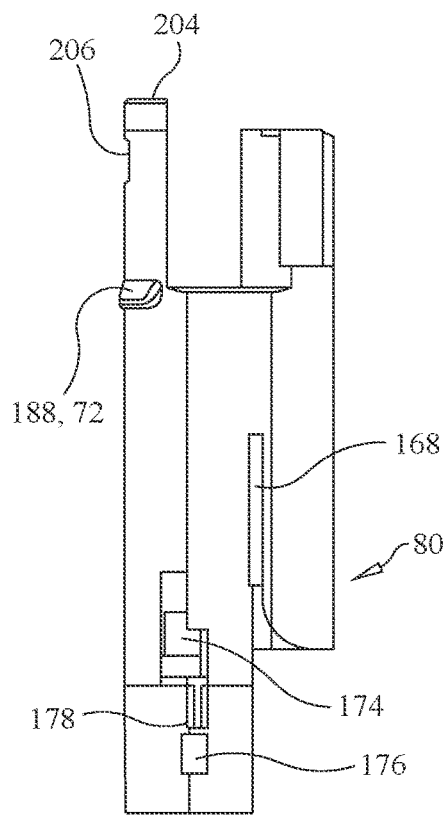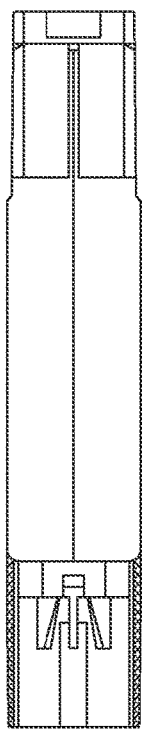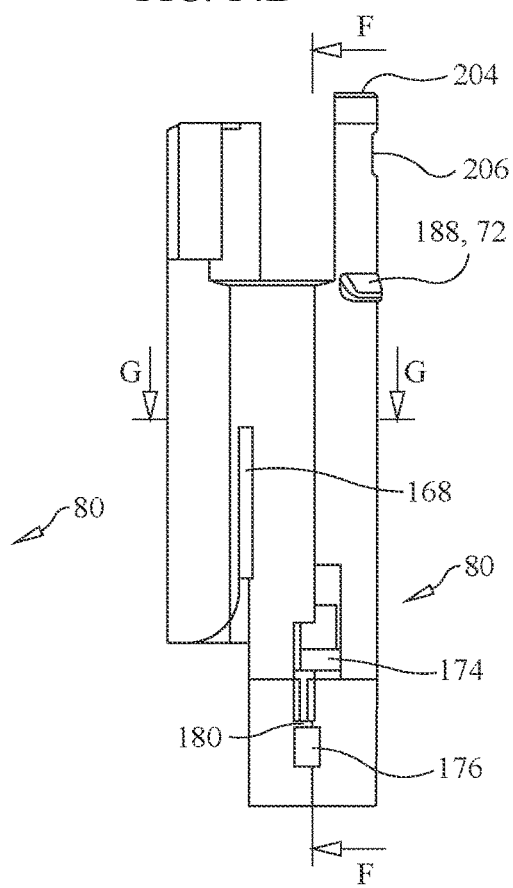
FIG. 14C  FIG. 14D  FIG. 14E

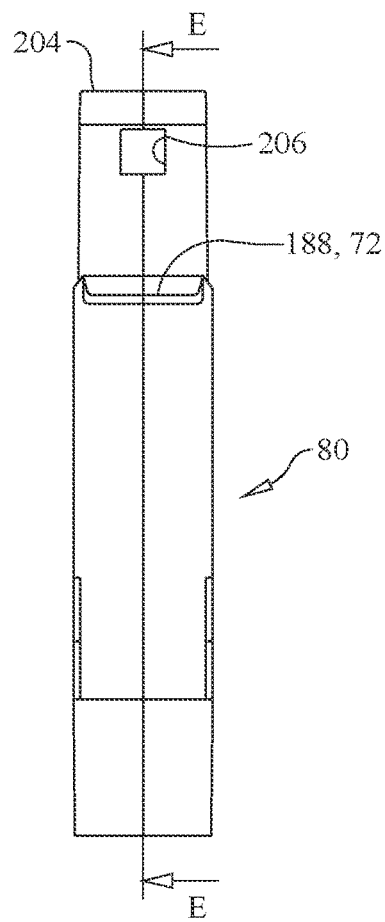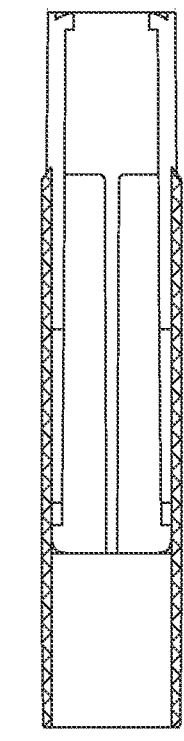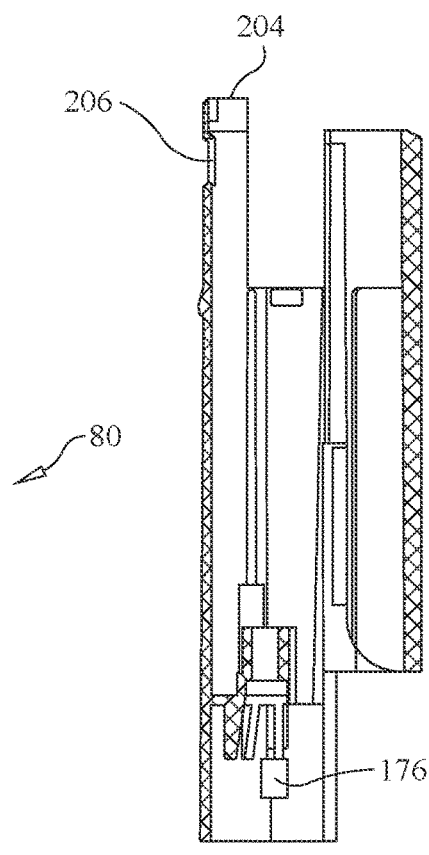
FIG. 14F  FIG. 14G  FIG. 14H
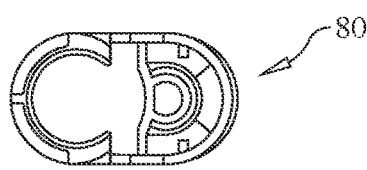
FIG. 14I
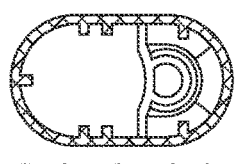
SECTION G-G
FIG. 14J

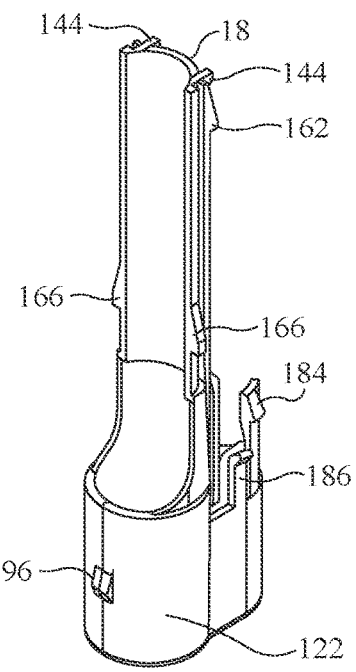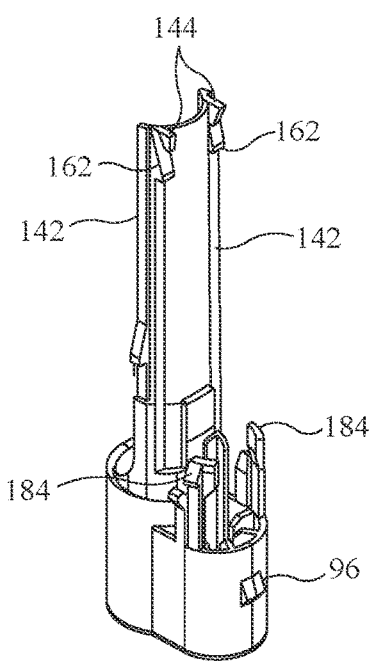
FIG. 15A  FIG. 15B
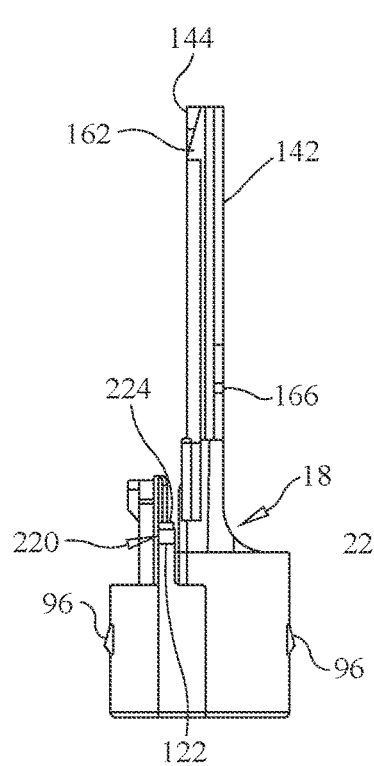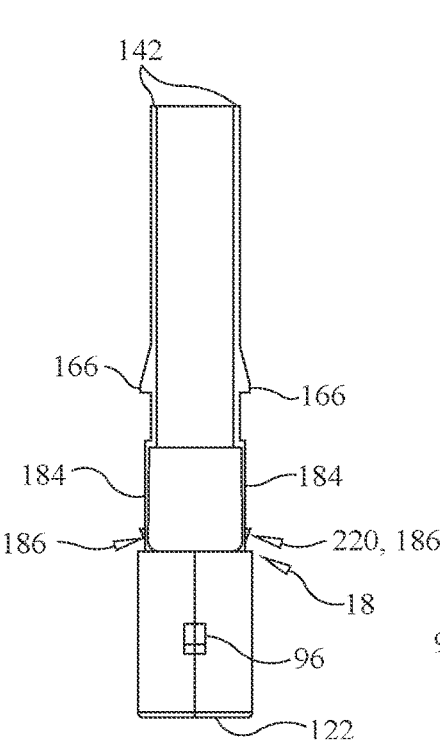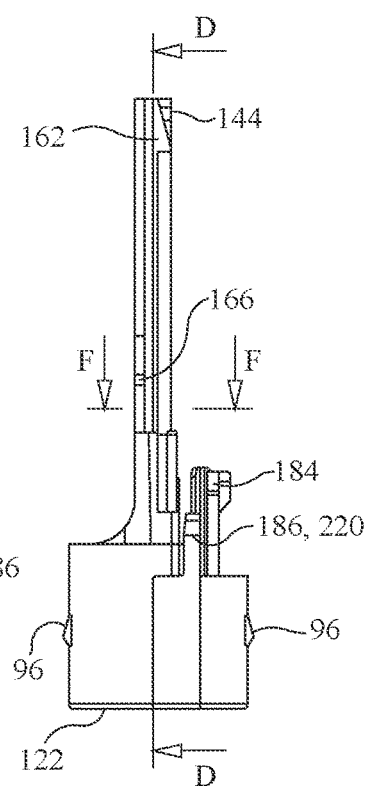
FIG. 15C  FIG. 15D  FIG. 15E

SECTION D-D

SECTION E-E

SECTION F-F

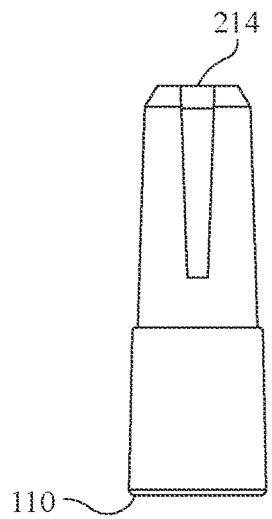
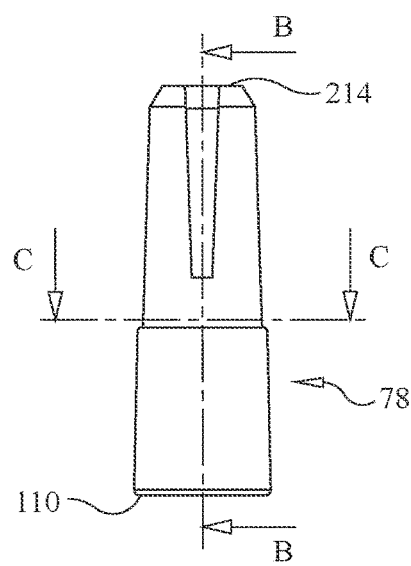
FIG. 16F    FIG. 16G
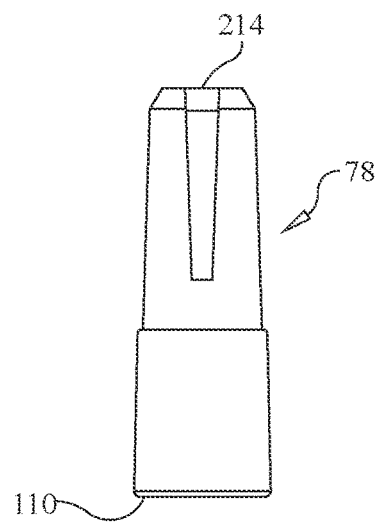
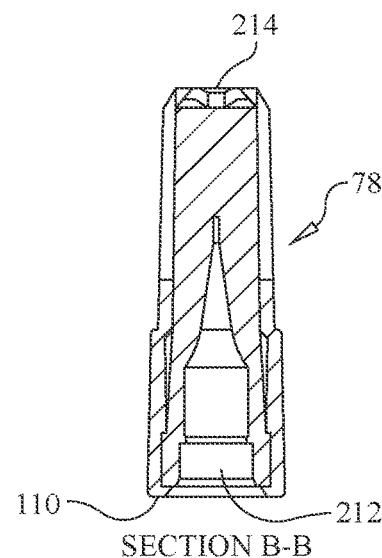
FIG. 16H    FIG. 16I
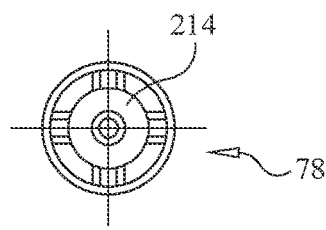
FIG. 16J    FIG. 16K

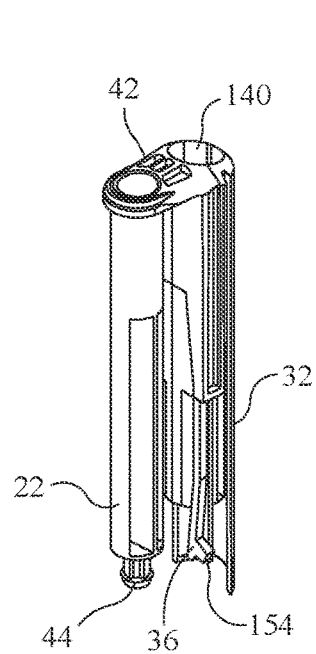 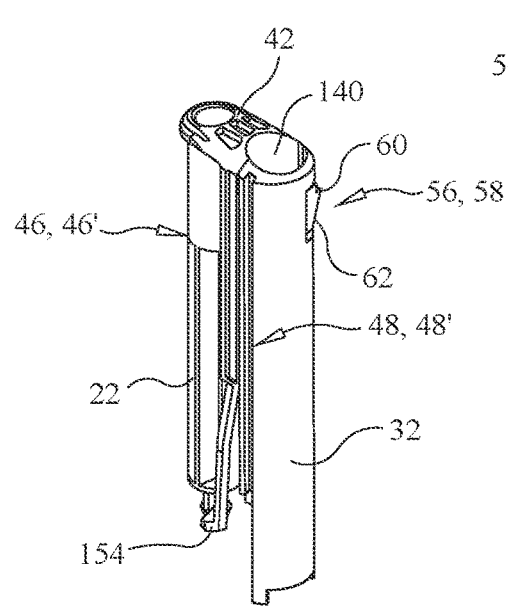 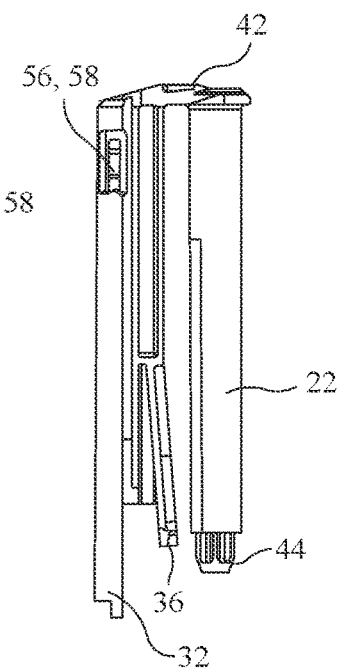
FIG. 17A  FIG. 17B  FIG. 17C
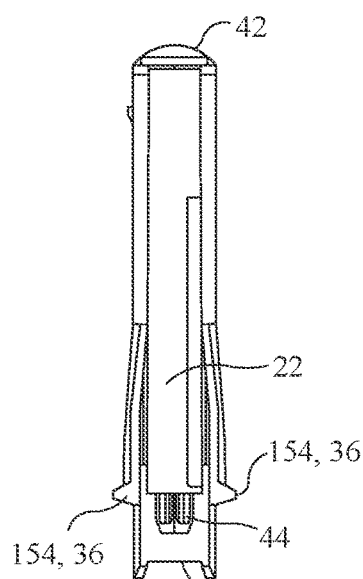 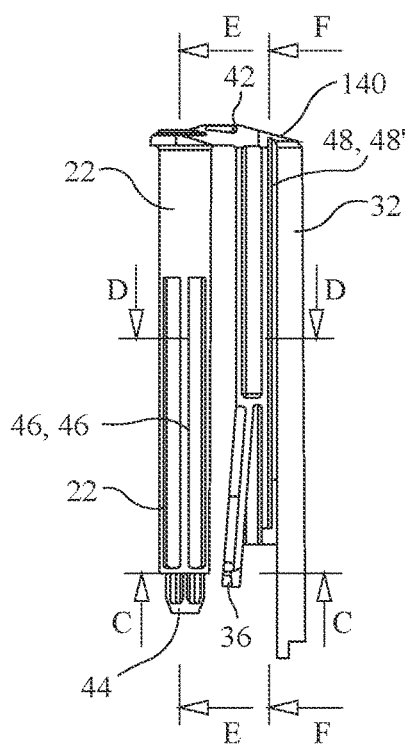 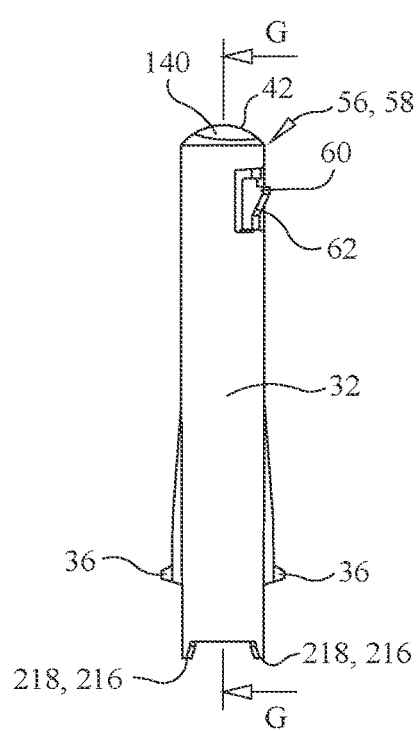
FIG. 17D  FIG. 17E  FIG. 17F

SECTION E-E

SECTION F-F

SECTION G-G

SECTION D-D

SECTION C-C

AUTOINJECTOR

CROSS-REFERENCE TO RELATED APPLICATION

This application claims priority to European Patent Application No. 21205088.4, filed on Oct. 27, 2021, the contents of which are hereby incorporated herein by reference in their entirety.

BACKGROUND

Field of the Invention

The present disclosure relates to an autoinjector comprising a housing and a drive chassis arranged linearly moveable within the housing, the drive chassis comprising a dispensing limb and a trigger limb, wherein the trigger limb and the dispensing limb are arranged in parallel to one another respectively at least essentially in parallel to one another and are connected to one another at a respective distal end of the dispensing limb and the trigger limb.

Background of the Invention

Conventional autoinjectors are typically disposable devices configured to dispense medicament from a pre-filled syringe. Such devices are single-use and intended for administration by a patient (i.e. self-administration) or carer. At point of use, the user removes a protective cap from the proximal end of the autoinjector and positions the autoinjector at the injection site (typically the skin of the thigh or belly) and presses the autoinjector axially in a proximal direction, to achieve needle insertion of a needle of the pre-filled syringe into the skin and to initiate dispense.

SUMMARY

It is an object of the present disclosure to make available an autoinjector formed from a very small number of low cost components and a very simple process, compared to the state of the art. It is a further object of the present disclosure to make available an as compact design as possible.

This object is satisfied by an autoinjector comprising the subject matter disclosed herein.

Such an autoinjector comprises a housing and a drive chassis arranged linearly moveable within the housing, the drive chassis comprising a dispensing limb and a trigger limb, wherein a plunger is arrangeable at a proximal end of the dispensing limb and a trigger arm is arranged extending proximally from the trigger limb, wherein the trigger limb and the dispensing limb are arranged in parallel to one another respectively at least essentially in parallel to one another and are connected to one another at a respective distal end of the dispensing limb and the trigger limb.

Due to the disposable nature of single-use auto-injectors, it is considered advantageous to minimise autoinjector complexity, material usage, package size and assembly complexity in this way, as this all tends to reduce cost and environmental impact, this is achieved by the autoinjector presented herein.

This is especially achieved by a reduction in the size of the device achieved by the parallel arrangement of the trigger limb and the dispensing limb of the drive chassis thereby leading to a reduction of the volume of raw materials used.

Moreover, since fewer parts are used one can reduce the cost of manufacturing equipment and simplify the assembly process.

Smaller devices also lead to a reduction of the volume required in transport and storage, which can be particularly expensive when low temperatures are required. This also reduces the carbon footprint associated with such autoinjectors.

In this connection it should be noted that the drive chassis is a component that can be configured to move in a straight line within the housing in order to drive a medicament stored in a pre-filled syringe arranged within the housing out of the pre-filled syringe on activation of the autoinjector by entraining the plunger of the pre-filled syringe in a manner known per se.

In this connection the dispensing limb can be a component of the drive chassis associated with dispensing the medicament from the pre-filled syringe, i.e. it can form a plunger rod, a plunger support or the like.

In this connection the trigger limb can be a component of the drive chassis associated with the process of triggering the autoinjector for a release of the drive chassis prior to dispensing the medicament, i.e. a component of the drive chassis cooperating with a release mechanism of the autoinjector.

In this connection the trigger arm can be a component of the release mechanism or a component that cooperates with the release mechanism of the autoinjector.

In this connection it should further be noted that the trigger arm can also extend in the radial and/or transverse direction relative to the trigger limb.

By forming the trigger limb and the dispensing limb in parallel to one another construction space can be saved as the prior art plunger limbs can be reduced significantly in length.

Moreover, forming a drive chassis in the aforementioned way also reduces the number of components as various functions of the drive chassis described herein are associated with individual parts in prior art drive chassis.

The trigger limb, the dispensing limb, the plunger and the trigger arm can be integrally formed in one piece. In this way a single component made of one and the same material can be made available with the single component being configured to carry out various functions for which individual components are required in prior art devices.

The trigger arm can be biased with respect to the housing of the autoinjector in a storage state of the autoinjector. The trigger arm can be a component of a release mechanism of the autoinjector configured to engage and disengage a further component in dependence on the state of use of the autoinjector, e.g. the storage state, the dispensing state and/or the lock-out state. On releasing this bias of the trigger arm, the autoinjector can be moved from the storage state to the dispensing state.

The trigger arm can be configured to be deflected relative to the housing and optionally relative to the trigger limb upon moving the autoinjector from a storage state into a dispensing state of the autoinjector. In this way a component of the release mechanism can be moved in order to initiate a dispensing process of the autoinjector.

The autoinjector can further comprise a needle guard, wherein the trigger arm is actuated on by the needle guard of the autoinjector upon moving the autoinjector from a storage state into a dispensing state of the autoinjector. In this way the design of the autoinjector can be further simplified and a further part of the autoinjector can have several functions associated therewith. The functions of the needle guard, on the one hand, are to guard a needle of the autoinjector before and after use, and, on the other hand, to form a part of the release mechanism of the autoinjector.

An outer surface of the trigger limb can comprise a first and a second part outer surface whose appearance differ from one another. In this way a visual communication of the end of the dose can be made available at the autoinjector using the drive chassis.

The autoinjector can further comprise a drive spring, wherein the drive spring can be arranged within the housing of the autoinjector between a distal housing wall and the drive chassis. The drive spring is utilized to automatically drive the medicament out of the autoinjector once the release mechanism of the autoinjector has been engaged and the spring bias is automatically released.

In this connection it should be noted that the drive spring can be biased with respect to the housing in the storage state of the autoinjector.

The drive spring can also bias the trigger arm in a storage state of the autoinjector with respect to the housing of the autoinjector. In this way a further component of the autoinjector can be used to satisfy several functions. Moreover, the inherent force stored in the drive spring can be used to lock the autoinjector prior to use thereof.

The trigger limb can be configured to receive at least a part of the drive spring. In this way the design of the autoinjector can be made as compact as possible and a length thereof can be reduced even further. By way of example, the trigger limb can comprise a passage configured to receive at least a part of the drive spring.

The drive spring can be configured to drive the plunger of the autoinjector into a pre-filled syringe of the autoinjector. In this connection it should be noted that the drive spring is arranged in parallel to, i.e. axially offset from the plunger of the pre-filled syringe.

The drive chassis can be linearly guided within the housing upon moving the autoinjector from a storage state into a dispensing state of the autoinjector. By guiding the drive chassis within the housing a movement direction of the components of the autoinjector can be pre-defined and a frictional engagement of the parts can be tailored to one another.

The trigger arm can be configured to move radially and transversely with respect to the trigger limb. This provides several degrees of freedom regarding the movement of the trigger arm.

The trigger arm can be configured to cooperate with a stop feature arranged at the housing in a storage state of the autoinjector. In this way a release mechanism can be formed between the drive chassis and the housing of the autoinjector leading to a further reduction in the size and components of the autoinjector.

The trigger limb and the dispensing limb can be arranged in an at least generally U-shaped manner respectively in a U-shaped manner. Such a U-shaped design of the autoinjector leads to a reduction in the size of the autoinjector.

In this connection it should be noted that the trigger limb and the dispensing limb are arranged to extend, at least approximately, in the same direction starting from the web, axially offset from one another.

The trigger limb can further comprise at least a first part of an audible end of dose feedback member. In this way an audible communication can be given to a user upon use of the autoinjector. Moreover, the drive chassis can satisfy a further function leading to a reduced size of the autoinjector.

The housing can optionally comprise at least a second part of the audible end of dose feedback member. In this way the design can be simplified and made more compact.

The first and second parts of the audible end of dose feedback members can be formed by an opening and a latching tongue configured to engage the opening. Such a component is simple in design, requires few parts and is simple to implement.

The audible end of dose feedback member can be configured to emit a sound once the material has been dispensed from the autoinjector. In this way an end of dose can be indicated to a user such that a user obtains feedback on a point in time where the autoinjector can be safely removed from the injection site with the knowledge that all medicament has been expelled.

The audible end of dose feedback member can be configured to emit a sound between the drive chassis and the housing once the material has been dispensed from the autoinjector. In this way the sound can be emitted between two parts moveable relative to one another in an as compact a design as possible.

BRIEF DESCRIPTION OF THE DRAWINGS

FIG. 11A is a part sectional view of an audible feedback member of the autoinjector in the dispensing state at end of dose, and FIG. 11B is an enlarged view of the audible feedback member of the autoinjector in the dispensing state at the end of dose;

FIGS. 12A to 12F illustrate various views of an example of a cap of an autoinjector;

FIGS. 13A to 13J illustrate various views of an example of an outer body of an autoinjector;

FIGS. 14A to 14J illustrate various views of an example of an inner body of an autoinjector;

FIGS. 15A to 15J illustrate various views of an example of a needle guard of an autoinjector;

FIGS. 16A to 16K illustrate various views of an example of a needle shield of an autoinjector; and FIGS. 17A to 17L illustrate various views of an example of a drive chassis of an autoinjector.

DETAILED DESCRIPTION

Figure 1A:
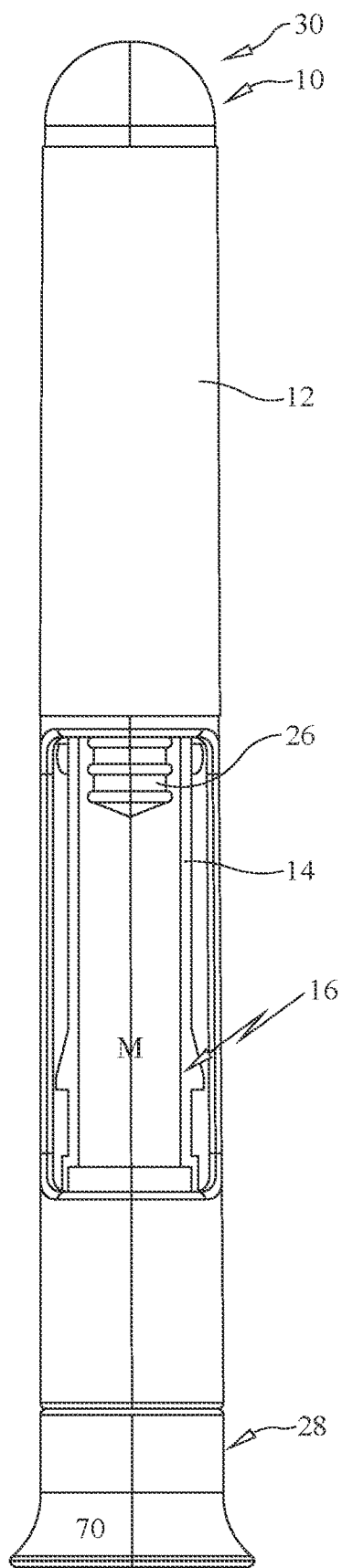
FIG. 1A is a side view of an autoinjector in a storage state.

References made in the following regarding directions are made in the context of the drawing and can naturally vary if the viewing position is changed. Moreover, similar parts or parts having similar functions will be referred to in the following using the same feature and/or reference numeral.

Figure 1B:
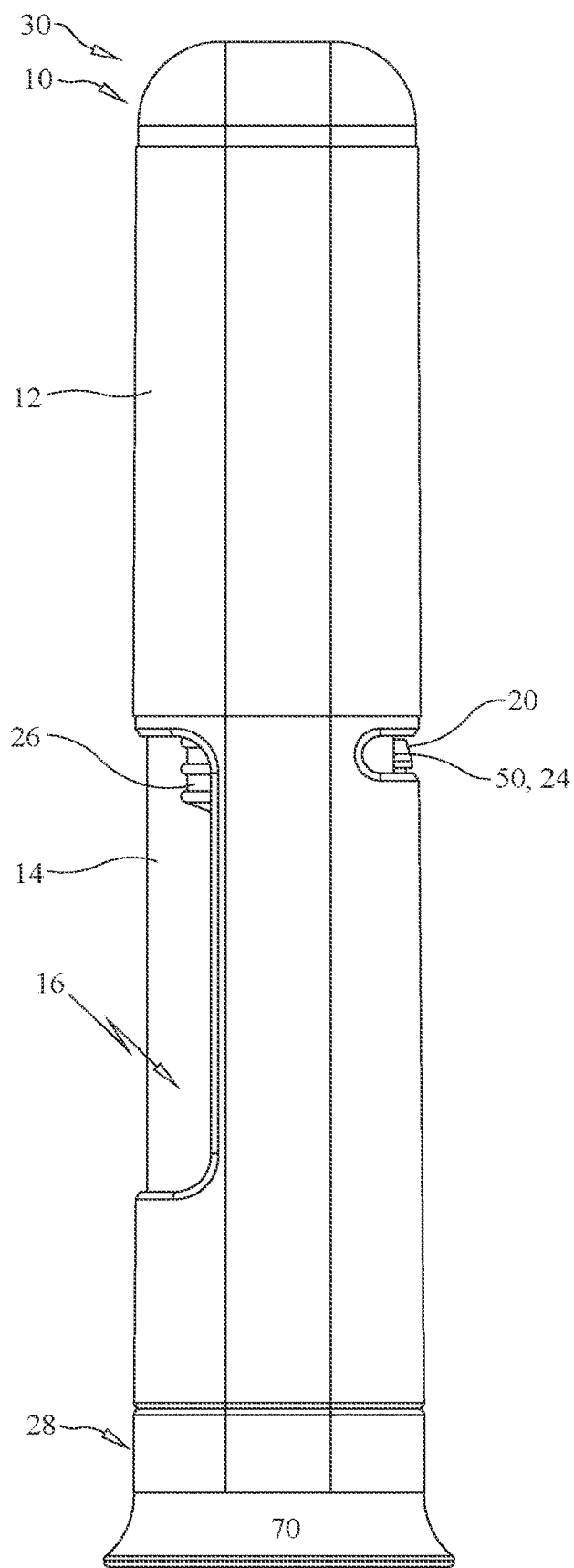
FIG. 1B is a further side view of the autoinjector of FIG. 1A in the storage state.

FIGS. 1A and 1B show side views of an autoinjector 10. The autoinjector 10 is a medical instrument that serves the purpose of administering a single dose of medicament M. The autoinjector 10 can not only be used by medical staff, but also by a patient themselves to administer the medicament M.

The autoinjector 10 has a housing 12 with a syringe window 14 (see FIG. 1A) present therein. A pre-filled syringe 16 is arranged within the housing 12 and visible via the syringe window 14. The pre-filled syringe 16 is filled with the medicament M.

A needle guard 18 (see e.g. FIG. 2A) is arranged at a proximal end 28 of the autoinjector 10. The needle guard 18 has the function of protecting a patient from a needle 34 (see e.g. FIG. 3B) before and after use of the autoinjector, i.e. in a storage state and in a lock-out state of the autoinjector 10.

In this connection it should be noted that the terms proximal and distal refer to the position of the needle 34 relative to a patient with proximal meaning closest to a main mass of the body of a patient and distal meaning it is more distant from the main mass of the body of a patient.

FIG. 1B shows a status indicator window 20 in which a first part outer surface 50 of a drive chassis 24 of the autoinjector 10 is visible.

A cap 70 is arranged at the proximal end 28 of the autoinjector 10 disposed opposite to a distal end 30 of the autoinjector 10. The cap 70 covers both the needle 34 and the needle guard 18 in the storage state of the autoinjector 10.

Figures 2A, 2B:
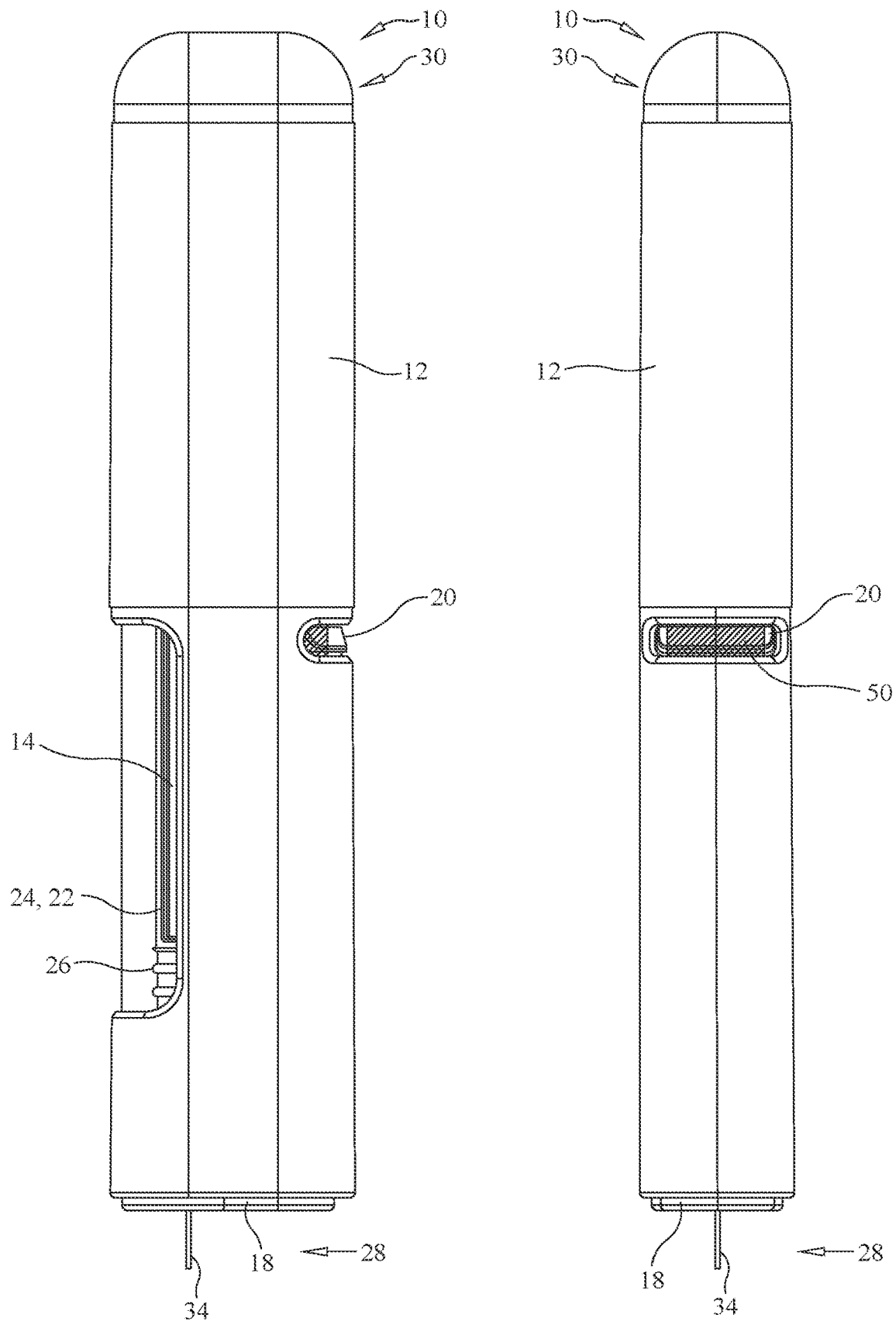
FIG. 2A is a side view of the autoinjector of FIG. 1A in a dispensing state.
FIG. 2B is a further side view of the autoinjector of FIG. 1A in the dispensing state.

FIGS. 2A and 2B show the autoinjector 10 of FIGS. 1A and 1B with the cap 70 removed and the needle guard 18 moved distally, i.e. moved away from the proximal end 28, and into the autoinjector 10. The distal movement of the needle guard 18 into the autoinjector also brings about an engagement of a release mechanism 40 (see e.g. FIGS. 4A, 4B and 4C).

On engaging the release mechanism 40, the drive chassis 24 (see also FIG. 3) is moved proximally and a dispensing limb 22 thereof moves a plunger 26 through the pre-filled syringe 16 in order to dispense the medicament M via the needle 34.

In this connection it should be noted that the plunger 26 can be a part separate from the dispensing limb 22 and can be pre-arranged within the pre-filled syringe and configured to be engaged by the dispensing limb 22.

In other designs of the autoinjector 10, the plunger 26 can be a part of the dispensing limb 22.

FIG. 2A shows the presence of the dispensing limb 22, the drive chassis 24 and the plunger 26 in the syringe window 14 following the movement of the drive chassis 24 in the proximal direction, i.e. at an end of dose state of the autoinjector 10.

FIG. 2B shows a second part outer surface 52 of the drive chassis in the status indicator window 20.

In the drawings shown above, the status indicator window 20 on the side of autoinjector 10 shows a device status in clear, binary form, which is likely to be very useful particularly to naïve users. Before (and possibly during) dispense, the colour displayed through the window is printed on the drive chassis 24 (see also FIG. 3. At the end of the dispense, the moulded colour (indicated with the hashed lines) of the drive chassis 24 is displayed through the status indicator window 20. Other configurations of display, for example employing graphics to indicate that dispense is in progress, icons or text, are possible.

Moreover, before dispensing, the dispensable fluid volume of the medicament M is clearly visible through the syringe window 14 that is formed as a large wrap-around window in the housing 12. The geometry of this window 14 is intended to maximise the viewing angle for the user.

The progress of the dispense can also be viewed through the window 20 as a movement of the plunger 26 and of the drive chassis 24 is visible through the syringe window 14.

At the end of dispense, the syringe window 14 is filled with the drive chassis 24 and the plunger 26 to provide additional visual indication that the autoinjector 10 has been used. This means that two forms of different visual indication of the end of dose are present. The part of the drive chassis 24 visible through the syringe window 14 could include a surface decoration or marking, e.g. printed in a different colour to provide further visual communication of the end of the dose.

Figure 3:
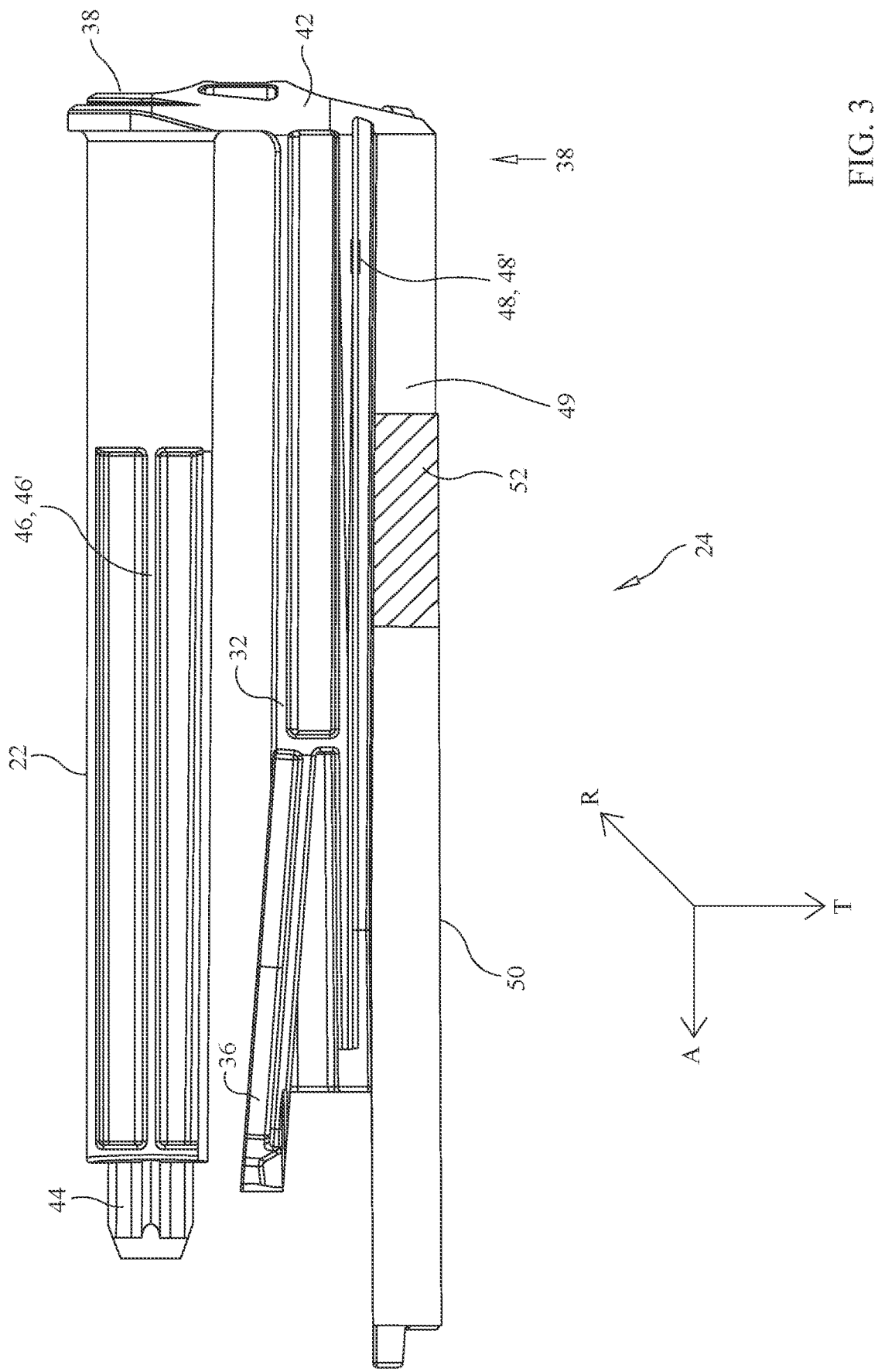
FIG. 3 is a side view of a drive chassis for an autoinjector.

FIG. 3 shows the drive chassis 24. The drive chassis 34 comprises the dispensing limb 22 and a trigger limb 32. The trigger limb 32 and the dispensing limb 22 are arranged in parallel to one another. The drive chassis 24 is a component that is configured to move in a straight line within the housing in order to drive the medicament M out of the pre-filled syringe on activation of the autoinjector 10.

The trigger limb 32 and the dispensing limb 22 are arranged in an at least generally U-shaped manner respectively in a U-shaped manner and are connected to one another at a distal end 38 of the drive chassis 24 via a web 42, i.e. axially offset from one another in the transverse direction T with a length of the trigger limb 32 being longer than a length of the dispensing limb 22.

In this connection it should be noted that in other designs the dispensing limb 22 can also have the same length as the trigger limb 32 or even be longer than the trigger limb 32.

A plunger support 44 is arranged at an end of the dispensing limb 22 remote from the web 42. The plunger support 44 is configured to engage the plunger 26 that moves through the pre-filled syringe 16, i.e. the plunger support 44 is configured to act on the pre-filled syringe 16 of the autoinjector 10 via the plunger 26 that is arranged within the pre-filled syringe 16.

A trigger arm 36 is arranged to extend proximally from the trigger limb 32 in both a transvers direction T and a radial direction R relative to an axial direction A, with the axial direction A extending in parallel to the trigger limb 32. The trigger arm 36 is arranged extending from the trigger limb 32 in a direction remote from the distal end 38.

The trigger arm 36 is fixedly attached to the trigger limb 32 and moveable relative to the trigger limb 32.

The trigger arm 36 is connected to the trigger limb at a position corresponding to a length of the trigger limb 32 corresponding to 20 to 80% of a length of the trigger limb 32 from the distal end 38.

In this connection it should be noted that the drive chassis 24 is formed in one piece, i.e. the trigger limb 32, the dispensing limb 22, the plunger support 44 and the trigger arm 36 are integrally formed in one piece, preferably from one and the same material, e.g. in the same injection mold, or, if manufactured by additive manufacturing techniques, in one production cycle.

The drive chassis 24 can be installed in the autoinjector 10 shown in connection with FIGS. 1A and 1B and 2A and 2B. The drive chassis 24 may then be linearly guided within the housing 12 of the autoinjector upon moving 10 the autoinjector 10 from a storage state into a dispensing state of the autoinjector.

For this purpose the drive chassis 24 can have first and second guiding aids 46, 48 cooperating with corresponding structures present within the housing 12. In the present example the first and second guiding aids 46, 48 are formed by first and second grooves 46', 48' that respectively extend in the axial direction A along the dispensing limb 22 respectively the trigger limb 32. The first and second grooves 46', 48' cooperate with lugs 164, 228 (see e.g. FIG. 10A respectively FIG. 13G) present on an inside wall of the housing 12.

Alternatively the drive chassis 24 can comprise lugs cooperating with corresponding grooves in the housing 12 as the first and second guiding aids 46, 48.

Alternatively, the trigger limb 32 and the dispensing limb 22 can be shaped in such a way that they cooperate with guide structures present within the housing 12, by way of example, the trigger limb 32 and the dispensing limb 22 can have a round outer shape in a cross-section therethrough perpendicular to the axial direction A, with the round outer shapes of the trigger limb 32 and the dispensing limb 22 then being guided in complementary shaped parts of the housing 12.

Figure 4A:
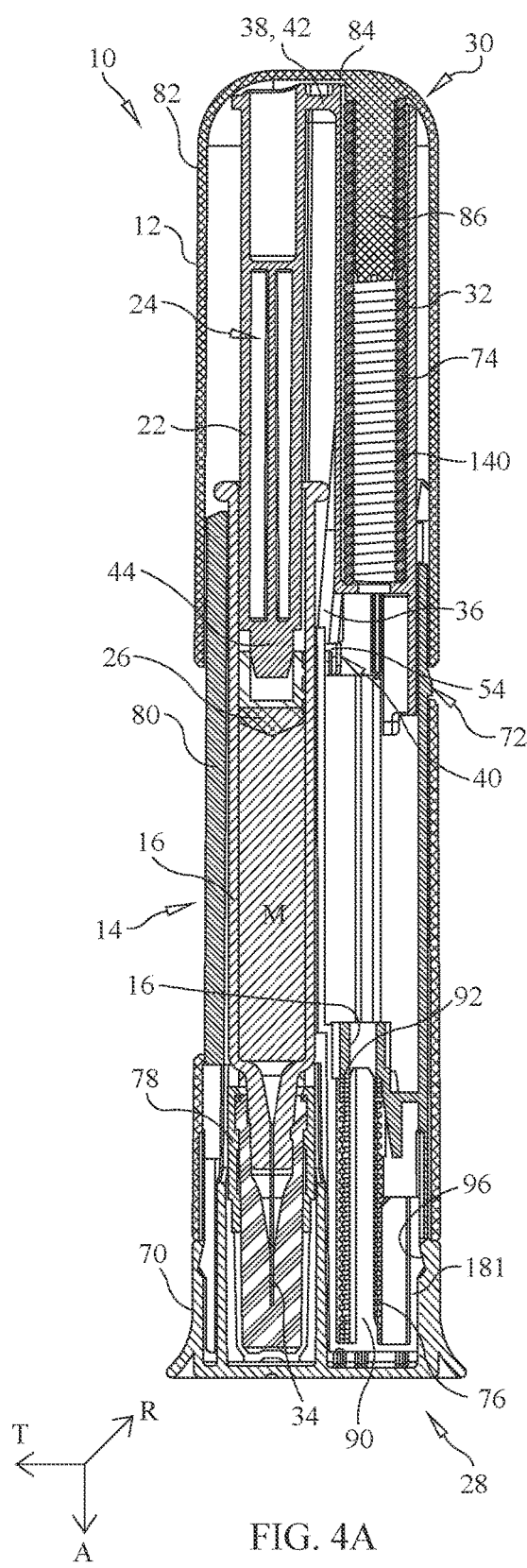
FIG. 4A is the autoinjector of FIG. 1A in the storage state.

In the storage state the trigger arm 36 is held at a stop feature 54 (see e.g. FIG. 4A). Upon moving the autoinjector from the storage state into the dispensing state of the autoinjector, the trigger arm 36 is deflected out of engagement from the stop feature 54. For this purpose the trigger arm 36 is moveable relative to the trigger limb 32, i.e. the position of the trigger arm 36 can be moved relative to the trigger limb 32.

In this connection it should be noted that the stop feature 54 is arranged at a height along the axial direction A of the housing 12 corresponding to a length of 45% of the length of the housing 12 from the distal end 30 of the autoinjector 10.

In this connection it should be noted that the stop feature 54 can be arranged at a height along the axial direction A of the housing 12 selected in the range of 30 to 70% of the length of the housing 12 from the distal end 30 of the autoinjector 10.

In this connection it should be noted that the trigger arm 36 is configured to move radially in the radial direction R and transversely in the transverse direction T with respect to the trigger limb 32.

The trigger limb 32 has an outer surface 49 comprising the first part outer surface 50 (hashed surface) and the second part outer surface 52 (black outer surface). The first and second part outer surfaces 50, 52 are present at a transverse side of the trigger limb 32, i.e. pointing in the transverse direction T. The first and second part outer surfaces 50, 52 are visible via the status indicator window 20 in different states of use of the autoinjector 10.

Specifically, as indicated in FIG. 1B, the first part outer surface 50 is visible via the status indicator window 20 in the storage state of the autoinjector 10 and the second part outer surface 52 is visible via the status indicator window 20 in the dispensing state towards an end of dose and in the lock-out state of the autoinjector 10 following an end of dose.

A first limb of the U-shaped drive chassis 24 is formed by the dispensing limb 22 and a second limb of the U-shapes drive chassis 24 is formed by the trigger limb 32.

A distal end of the syringe window 14 is arranged at approximately the same height as a distal end of the status indicator window 20. The syringe window 14 and the status indicator window 20 are arranged in a part of the housing 12 where an inner body 80 and an outer body 82 (see FIGS. 4A, 4B and 4C) overlap. The third part of the drive chassis 24 that may be visible in the syringe window 14 is the dispensing limb 22 in addition to which the plunger 26 of the pre-filled syringe 16 is also visible.

In this connection it should be noted that the first and second parts 50, 52 of the drive chassis 24 are not visible in the syringe window 14.

So that a user (not shown) can distinguish between the different states of use, i.e. between the first and second part outer surfaces 50, 52, the appearances of the first and second part outer surfaces 50, 52 differ from one another, i.e. these are different from one another.

In the present example the second part outer surface 52 comprises a marking printed thereon in the form of a hashed structure, other kinds of surface decorations and/or markings can be employed. The first part outer surface 50 is e.g. formed in the same colour as the remaining drive chassis 24, however, can also have some other colour comprise some form of surface marking and/or decoration or other form of visual indicator.

By way of example words such as "full and/or ready" and "empty and/or used" could printed on the first and second part outer surfaces 50, 52. Additionally and/or alternatively the first and second part outer surfaces 50, 52 can be coloured differently from one another, e.g. in red or green or the like.

Figure 4B:
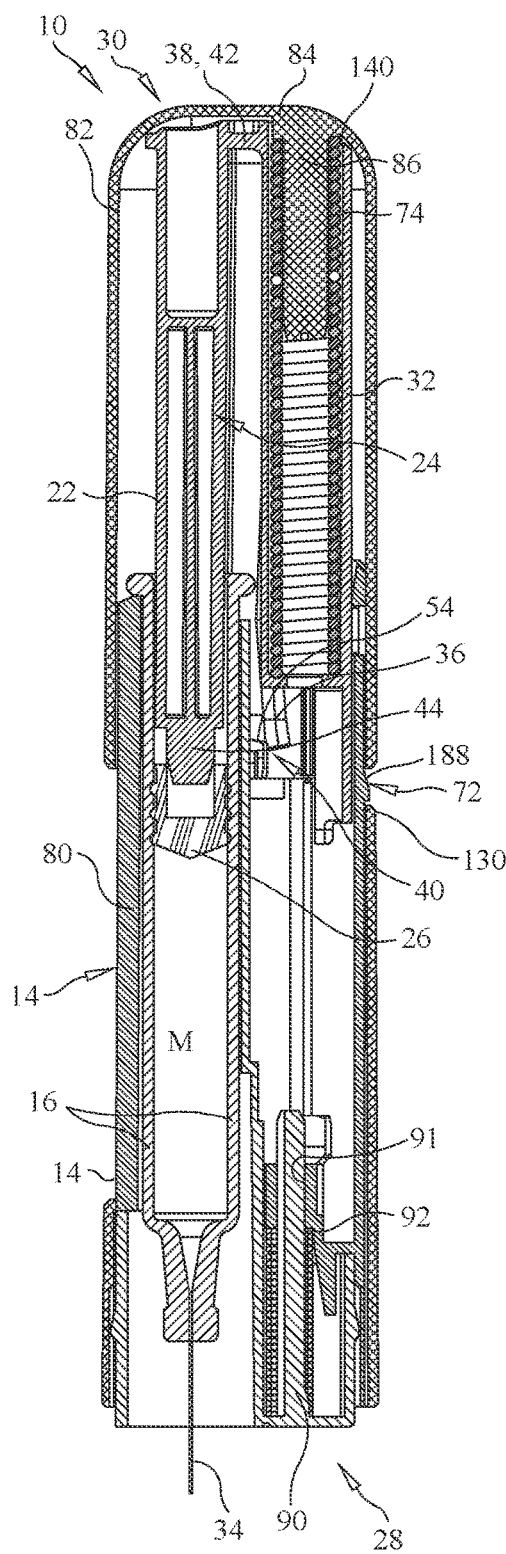
FIG. 4B is the autoinjector of FIG. 1A in the activated state shortly before the dispensing state.
Figure 4C:
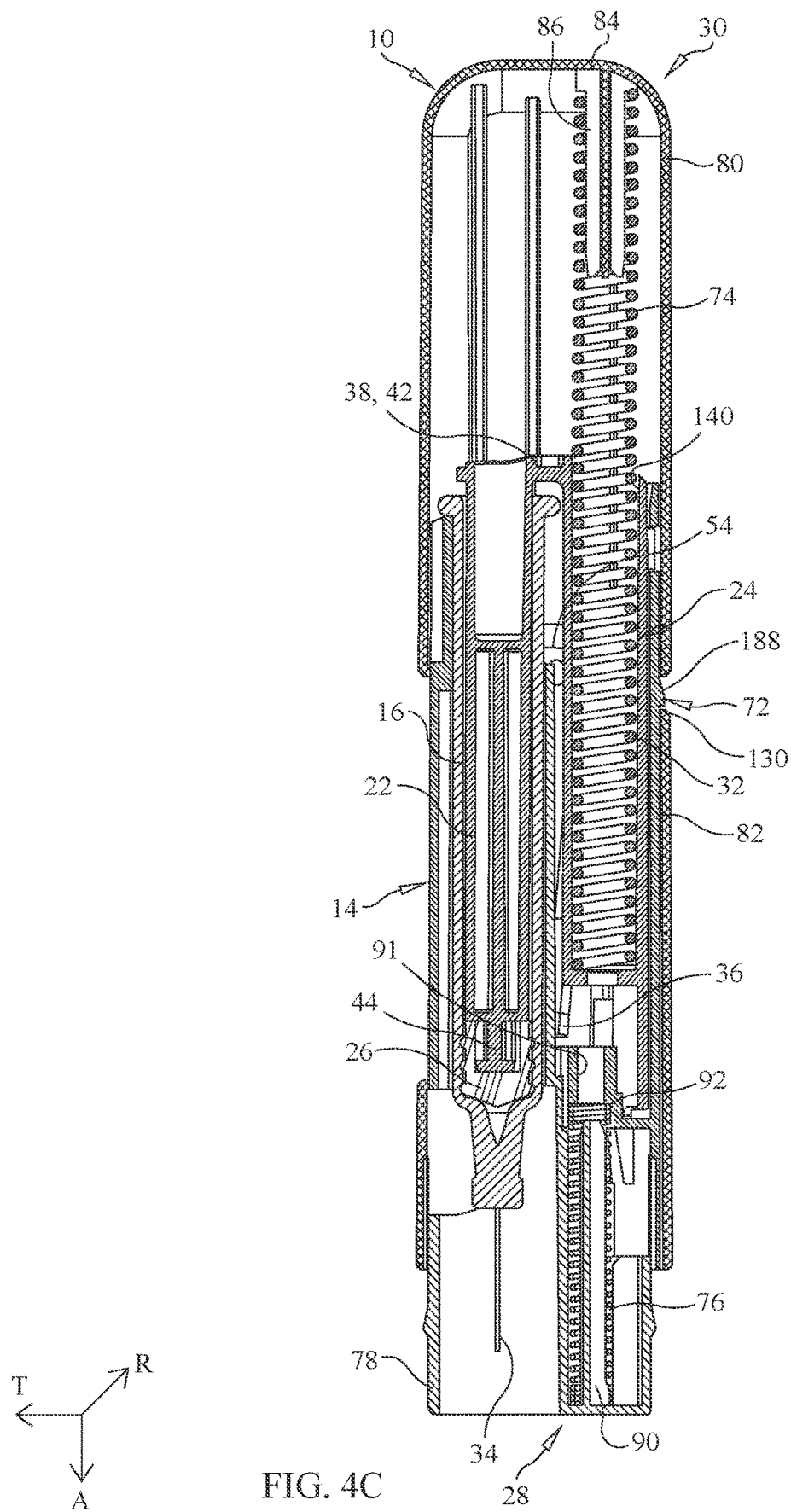
FIG. 4C is the autoinjector of FIG. 1A in a lock-out state.

The autoinjector 10 shown in FIGS. 4A to 4C comprises the needle guard 18 the removable cap (only FIG. 4A), the pre-filled syringe 16 arranged within the housing 12, a drive spring 74, a lock-out spring 76, and a removable needle shield 78 (RNS).

FIG. 4A shows the autoinjector 10 of FIG. 1A in the storage state, FIG. 4B shows the autoinjector 10 of FIG. 1A in the activated state shortly before the dispensing state, and FIG. 4C shows the autoinjector 10 of FIG. 1A in the lock-out state.

In the storage state of the autoinjector 10, a cap 70 is installed at the proximal end 28 of the autoinjector 10. On removal of the cap 70, the needle guard 18 of the autoinjector 10 becomes accessible.

The needle guard 18 is mounted axially moveable in the housing 12 for movement between the storage state, the dispensing state and the lock-out state. The needle guard 18 adopts different axial positions relative to the housing 12 in each one of the storage state, the dispensing state and the lock-out state.

As indicated in FIG. 4B, the needle guard 18 is moved in the distal direction along the axial direction A to make the needle 34 accessible from the outside, i.e. so that a patient can insert the needle 34 into his skin.

The needle guard 18 can be moved automatically in the distal direction along the axial direction A as the patient moves the autoinjector 10 towards the injection point, as the contact with the patients' skin will automatically move the needle guard into the housing 12 of the autoinjector 10. For this purpose the needle guard 18 is configured to be axially moved in the distal direction between the storage state and the dispensing state.

Upon moving the needle guard from the storage state into the dispensing state the lock-out spring 76 is biased between the needle guard 18 and an inner body 80 of the housing 12.

Once a medicament M has been administered, i.e. dispensed from the autoinjector 10, the needle guard 18 is configured to be axially moved in the proximal direction between the dispensing state and the lock-out state on removing the autoinjector 10 from the injection site. This movement of the needle guard 18 is automatically brought about by a relaxation of the lock-out spring 76.

The housing 12 is a two-part housing formed of the inner body 80 and an outer body 82 that are fixed in position relative to one another and that are snap fit to one another via a connection 72.

As shown in FIG. 4B, the connection 72 is formed by a nose 188 formed at the inner body that is configured to latch to a window 190 formed in the outer body 82.

In this connection it should be noted that the connection 72 can also be brought about via a different kind of connection. For example, the nose 188 can be formed at the outer body 82 and project towards the inner body 80 and engage the window 190 then formed at the inner body 80, alternatively different forms of connector can be used to form the connection 72.

The trigger arm 36 is actuated on by the needle guard 18 of the autoinjector 10 upon moving the autoinjector 10 from the storage state into the dispensing state of the autoinjector 10. As can be seen from a comparison of FIGS. 4A and 4B, the trigger arm 36 is deflected in the transverse direction T. Moreover, the trigger arm 36 is also deflected in the radial direction R.

The drive spring 74 is arranged within the housing 12 of the autoinjector 10. The drive spring 74 is specifically arranged between a distal housing wall 84 and the drive chassis 24. More specifically the drive spring 74 is arranged between the distal housing wall 84 of the outer body 82 and within the trigger limb 32 of the drive chassis 24. In order to fix a position of the drive spring 74 this can be arranged at a projection 86 projecting proximally from the distal housing wall 84 of the outer body 82.

The drive spring 74 is received within a passage 140 formed in the trigger limb 36 of the drive chassis 24. This means that the trigger limb 36 is configured to receive the drive spring 74. In the present example, the passage 140 has a cylindrical shape that is complementary to an outer shape of the drive spring 74.

As can be seen from a comparison of FIGS. 4A, and 4B with FIG. 4C the drive spring 74 is relaxed in comparison to the other two states in the lock-out state. This is because a release of the engagement between the trigger arm 36 and the stop feature 54 permits a proximal movement of the drive chassis 24 relative to the housing, i.e. relative to the inner and outer bodies 80, 82 under relaxation of the previously biased drive spring 74.

The drive spring 74 also biases the trigger arm 36 in the storage state of the autoinjector 10 with respect to the housing 12 of the autoinjector 10 by urging this against the stop feature 54 by the inherent spring bias of the drive spring 74.

The drive spring 74 is further configured to drive the plunger support 44 of the drive chassis of the autoinjector 10 into the pre-filled syringe 16. This is due to the fact that the drive chassis 24 is linearly guided within the housing 12 and is permitted to move proximally once the trigger arm 36 is released from its engagement with the stop feature 54.

The needle guard 18 surrounds the needle 34 of the pre-filled syringe 16 in the storage state and in the lock-out state. Once the cap 70 is removed and the autoinjector 10 has been moved into the dispensing state, the needle guard 18 does not surround the needle 34 of the pre-filled syringe 16.

As indicated in FIGS. 4A to 4C, the autoinjector 10 further comprises the lock-out spring 76 that is arranged between the needle guard 18 and the housing 12, more specifically between the inner body 80 and the needle guard 18.

The lock-out spring 76 is biased between an end wall 88 of the needle guard 18 and a proximal end 92 of the inner body 80. The end wall 88 is arranged proximally with respect to the inner body 80 and the drive chassis 24.

Moreover, the needle guard 18 comprises a projection 90 projecting distally from the proximal end 28. The lock-out spring 76 is arranged at the projection 90, in particular, the projection 90 projects into the lock-out spring 76.

The needle guard 18 is configured to compress the lock-out spring 76 upon moving between the storage state and the dispensing state. This is possible as the lock-out spring 76 abuts a proximal end 92 of the inner body 80 of the autoinjector 10 and the projection 90 is guided through an aperture 91 present in the inner body 80.

Following a use of the autoinjector 10 and removal of the autoinjector from an injection site, the needle guard 18 is configured to be moved by a relaxation of the lock-out spring 76 between the dispensing state and the lock-out state in a proximal direction.

In this connection it should be noted that the projection 90 could also be disposed at the inner body 80 such that it projects towards the proximal end 28 of the needle guard 18. If this option is selected, then a length of the projection 90 has to be adapted such that the projection does not prevent movement of the needle guard in the distal direction and/or such that it does not project beyond the needle guard 18 in the dispensing state so as to not come into contact with a patient's skin, e.g. if it cooperates with an aperture (not shown) of the needle guard 18.

In the storage state of the autoinjector 10, the needle guard 18 is arranged at a first axial position. In the dispensing state the needle guard 18 is arranged at a second axial position and in the lock-out state the needle guard 18 is arranged at a third axial position. The first, second and third axial positions respectively differ from one another, with the third axial position being more proximal than the first and second axial positions and the first axial position being more proximal than the second axial position with respect to the housing 12.

In this connection it should be noted that the third axial position can be the same or very similar to the first axial position in other designs of the autoinjector 10.

This means that an outer length of the autoinjector 10 with the cap 70 removed is longest in the lock-out state, shortest in the dispensing state and of medium length in the storage state.

Figure 5A:
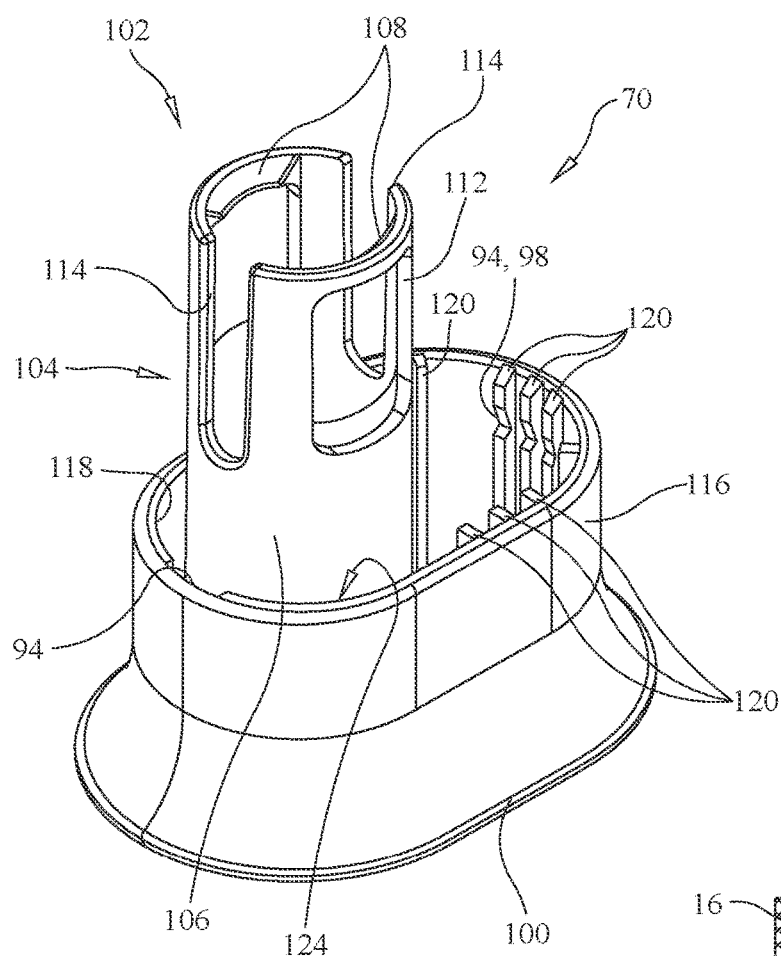
FIG. 5A is a view of a cap of the autoinjector.

FIG. 5A shows a perspective view of the removable cap 70. The cap 70 is of single piece design. The needle guard 18 is configured to cooperate with the cap 70 via one or more snap-fit connections 94, wherein each snap fit connection 94 comprises a protruding edge 96 (see e.g. FIG. 6) cooperating with a corresponding snap-fit area 98.

In this connection it should be noted that each of the following components can be respectively integrally formed in one piece, preferably from one and the same material, e.g.

in the same injection mold, namely the outer body 82, the inner body 80, the drive chassis 24, the needle guard 18, the cap 70, and/or the needle shield 78.

As shown in FIG. 5A, the removable cap 70 has a base 100. The cap 70 tapers outwardly in the region of the base 100 such that the base 100 of the cap 70 has a larger outer diameter than the remaining cap 70. This is particularly beneficial as the base 100 can act as a stand for the autoinjector 10 in the storage state of the autoinjector 10.

A needle guard facing end 102 of the cap 70 comprises a needle shield holder 104 at an end of the cap 70 disposed opposite to the base 100. The needle shield holder 104 is configured to hold the removable needle shield 78 covering the needle of the pre-filled syringe 16 in the storage state of the autoinjector 10.

The inner wall 106 of the needle shield holder 104 further comprises two windows 112. A respective one of the inwardly facing projections 108 is arranged at each of the windows 112.

Two recesses 114 are formed in the inner wall 106 of the needle shield holder 104 of the cap 70. The recesses are arranged between respective parts of the needle shield holder 104 having the windows 112.

The needle shield holder 104 projects distally from the base 100 of the cap 70 and is surrounded by an outer wall 116 of the cap 70. An inner surface 118 of the outer wall 116 of the cap 70 comprises several ribs 120.

Figure 5B:
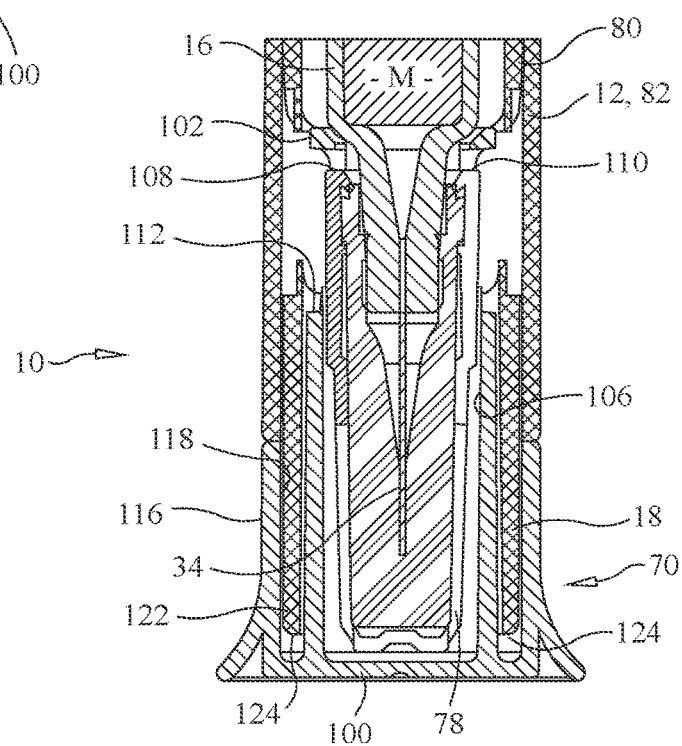
FIG. 5B is a sectional view of the autoinjector in the region where the cap of FIG. 5A is installed at the needle guard end of the autoinjector.

As indicated in FIG. 5B, a front end 122 of the needle guard 18 is arranged within an opening 124 of the cap 70. The opening 124 is formed between the outer wall 116 of the cap 70 and the needle shield holder 104.

The ribs 120 are configured to press radially inwardly, i.e. in the radial direction R, and transversely inwardly, i.e. in the transverse direction T, against the needle guard 18 in the storage state of the autoinjector 10.

As also shown in FIG. 5B the removable needle shield 78 is arranged within the needle shield holder 104. For this reason an inner wall 106 of the needle shield holder 104 comprises inwardly facing projections 108 at the needle guard facing end 102 that engage a syringe facing surface 110 of the needle shield 78.

Figure 6:
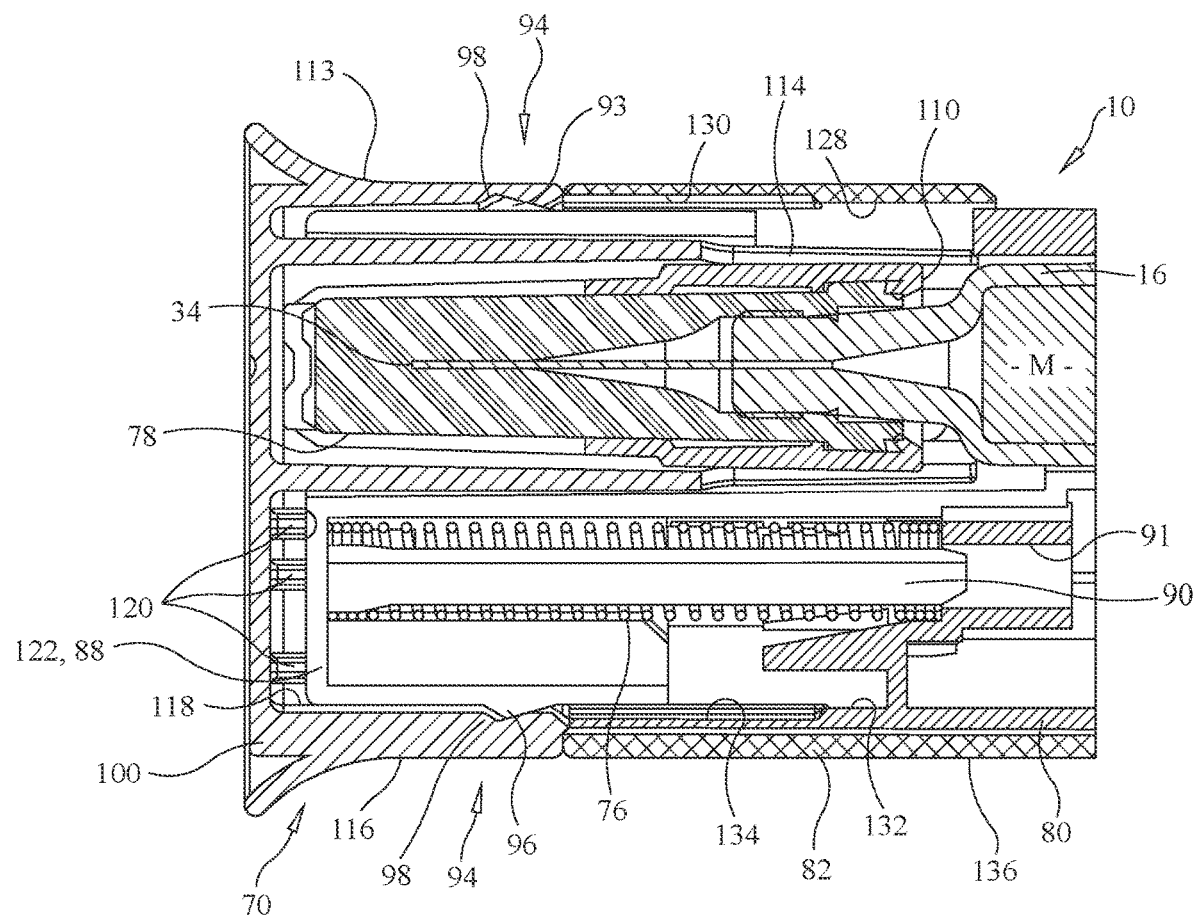
FIG. 6 is a part sectional view of the autoinjector showing the cap installed at the needle guard end of the autoinjector.

As indicated in FIG. 6 the protruding edges 96 are provided at an outer surface 126 of the needle guard 18. The snap-fit areas 98 are provided at the inner surface 118 of the cap 70.

The snap-fit connection 94 holds the cap 70 in place in the storage state of the autoinjector. The cap 70 is removably connected to the needle guard 18 and, on removal of the cap 70, the needle shield 78 is also removed from the autoinjector 10, as the projections 108 of the cap press on the syringe facing surface 110 of the removable needle shield 78 to entrain the removable needle shield in the proximal direction on removal of the cap 70.

In order to permit an as compact as possible design of the autoinjector 10, an inner surface 128 of the outer body 82 comprises a groove 130 in which one of the protruding edges 96 can axially move relative to the outer body 82 on an axial movement of the needle guard 18.

Similarly, an inner surface 132 of the inner body 80 comprises a further groove 134 in which a further one of the protruding edges 96 can axially move relative to the inner body 80 on an axial movement of the needle guard 18 relative to the housing 12.

The snap-fit projection 96 thereby forms detent features on the needle guard 18 that engage with corresponding features on the cap in order to provide a tight axial fit between the components following assembly.

A reverse arrangement of the detent features can also be possible, e.g. snap-fit areas can be present at the housing 12 and corresponding snap-fit projections could be present at the cap 70.

The proximal side of these detent features (snap-fit projections 96) on the needle guard is relatively steep, i.e. the proximal side of the snap-fit projections 96 is steeper than the distal side of the snap-fit projections 96 in the axial direction, so that once the cap 70 is removed, if the user attempts to re-attach it, the force to re-engage the detent features is high enough to cause the needle guard 18 to be moved distally until the detent features are hidden within the housing 12.

In this way, re-attachment of the detent features will not be possible (although the cap can be held in place by the engagement of the RNS 78 and the syringe glass). The distance by which the needle guard 18 is moved in order to hide the detent features is designed to be less than the distance required to trigger dispense, so that attempted re-attachment of the cap 70 in this way does not trigger dispense.

When the cap 70 is attached to the autoinjector 10, i.e. to the needle guard 18 via the snap-fit connection 94, the cap 70 prevents axial movement of the needle guard 18 when attached to the needle guard 18 in the storage state.

As further indicated in FIG. 6 the outer wall 116 of the cap 70 contacts an outer wall 136 of the housing 12 in the storage state of the autoinjector 10. The outer wall 116 of the cap 70 and the outer wall 136 of the housing 12 do not overlap in an axial direction A of the autoinjector 10. Moreover, the outer wall 116 of the cap 70 and the outer wall 136 of the housing 12 radially overlap in the storage state of the autoinjector 10.

It should be noted in this connection that the outer wall 136 of the housing is the outer wall 136 of the outer body 82 forming a part of the two-part housing 12.

Clip features in the form of the projections 108 on the cap 70 act on the distal surface of the rigid needle shield (RNS) 78 to grip onto it and remove it from the pre-filled syringe 16 when the cap 70 is pulled off by the user.

In this connection it should be noted that a 'three plate tool' construction can be used to mould the cap 70, including the clip features (projections 108) in a single component in a common injection mold (not shown) where state of the art devices typically construct similar caps from two or more separate components.

The projections 108 are supported by the needle guard 18 during removal of needle shield 78, helping to prevent them from splaying outwards and disengaging, as the needle shield holder 104 is biased radially inwardly by the needle guard 18.

Figure 7A:
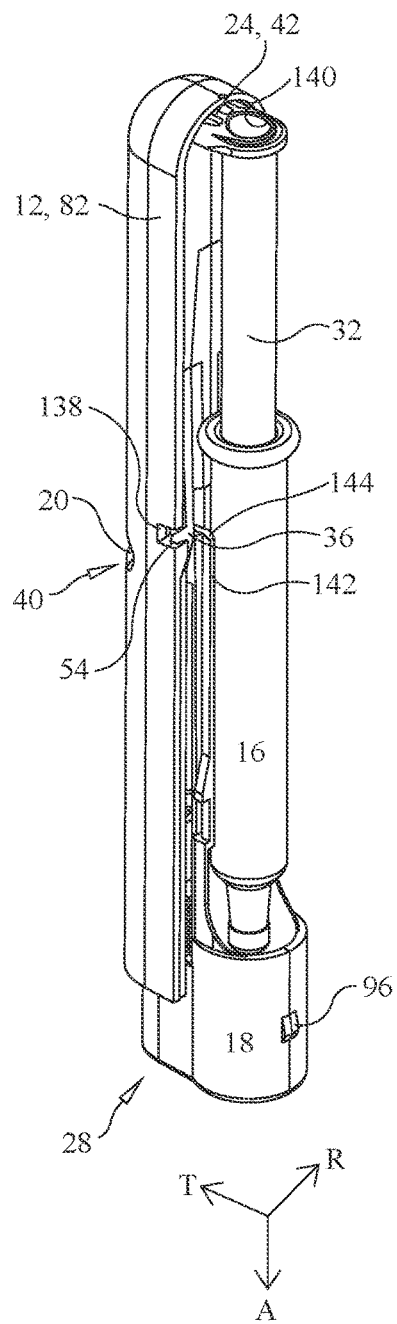
FIGS. 7A to 7C are part sectional views of the autoinjector, with a part of the housing removed, such that one can see components of a release mechanism of the autoinjector on activating the autoinjector.
Figure 7B:
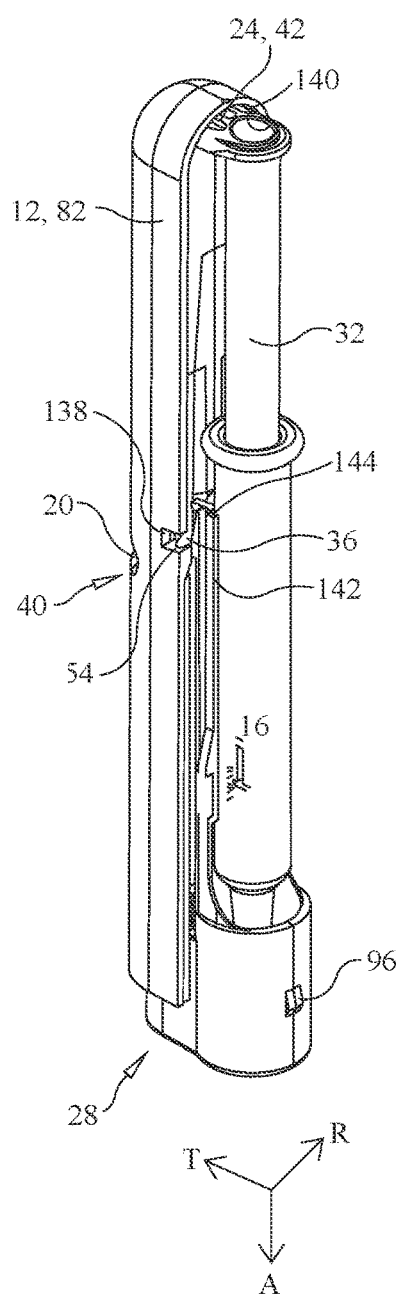
Figure 7C:
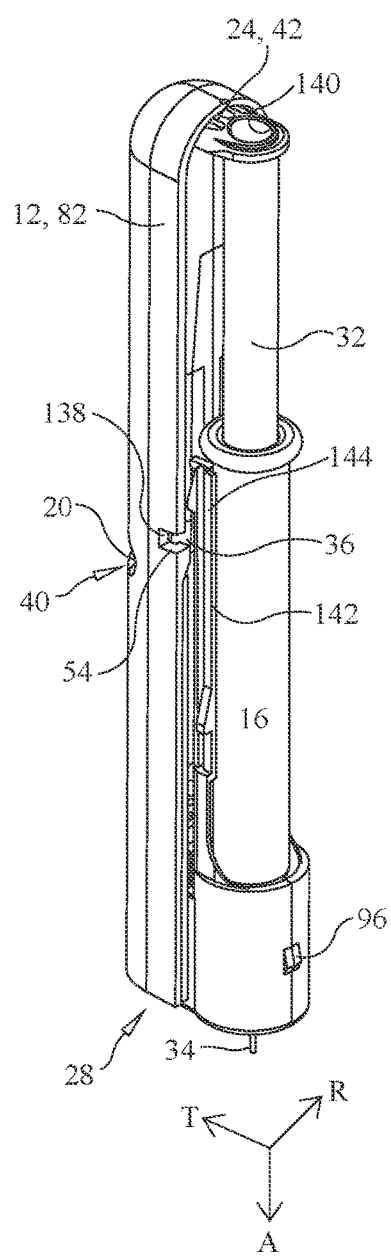

FIGS. 7A to 7C show part sectional views of the autoinjector 10, with a part of the housing 12 removed, such that one can see components of the needle guard 18, the drive chassis 24, the pre-filled syringe 16 and the housing 12 on activating the autoinjector 10.

These Figures illustrate a distal movement of the needle guard 18 into the housing 12 and how this then engages the release mechanism 40 comprising the trigger arm 36 and the stop feature 54 before the drive chassis 24 is moved proximally in order to administer the medication M stored in the pre-filled syringe 16.

The needle guard 18 comprises a plunger arm 142 as part of the release mechanism 40 of the autoinjector 10. The plunger arm 142 extends distally from the front end 122 of the needle guard 18.

As can be seen the relative position of the plunger arm 142 relative to the housing 12 varies and a distance the needle guard 18 projects beyond the housing 12 at the proximal end 28 reduces between FIGS. 7A to 7C.

Figure 8A:
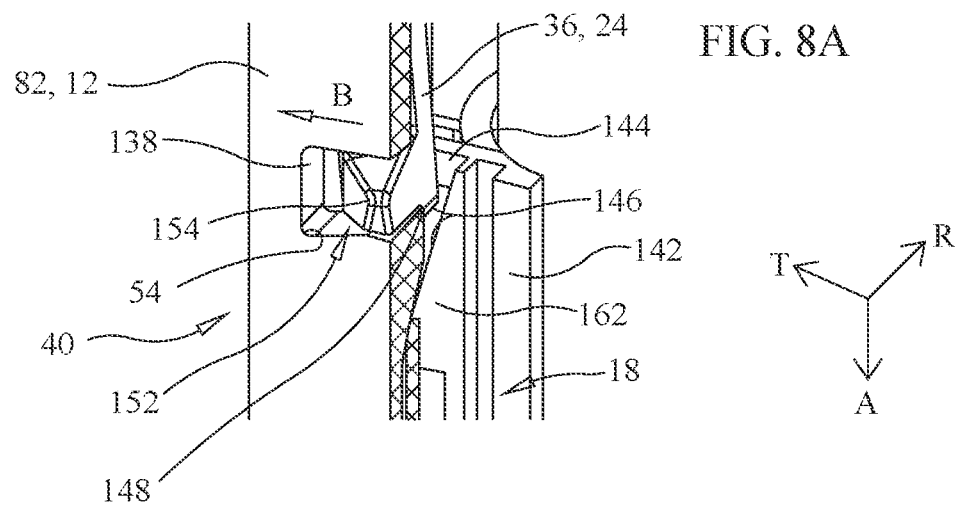
FIGS. 8A to 8C are detailed views of the release mechanism of the autoinjector of FIGS. 7A-7C.
Figure 8B:
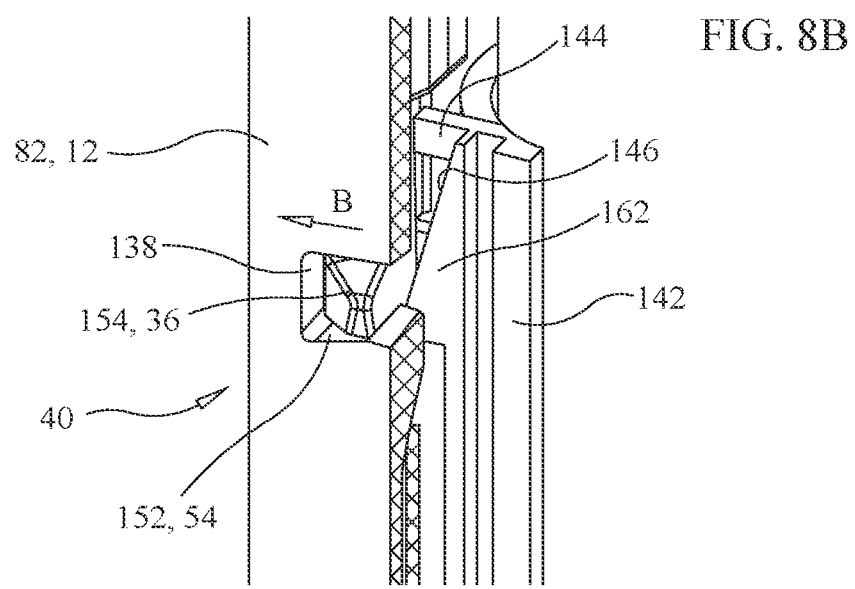
Figure 8C:
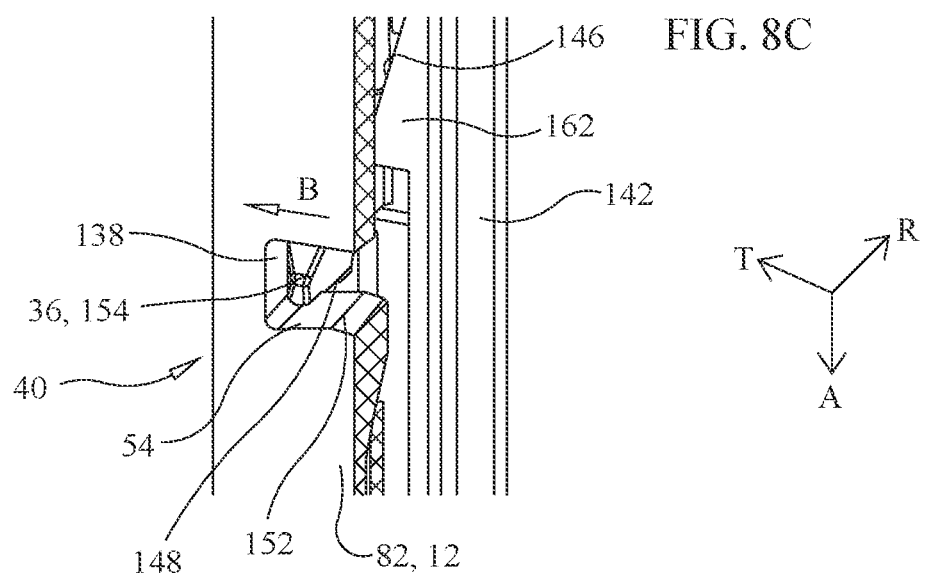

FIGS. 8A to 8C show detailed views of the different positions of the release mechanism 40 of the autoinjector 10 corresponding to the views shown in FIGS. 7A to 7C.

FIG. 8A shows an enlarged view of the components of the release mechanism 40 of the autoinjector 10 which comprises the trigger arm 36 of the drive chassis 24, and the stop feature 54 present in an opening 138 of the housing 12 with which the trigger arm 36 cooperates.

In this connection it should be noted that the opening 138 of the housing 12 is indicated as a through-going opening, i.e. it is open both at an outer wall of the housing 12 as well as an inner wall of the housing 12. It should however be noted that it can also be formed as a recess in the inner wall of the housing 12 such that it does not go through the wall of the housing 12.

The drive chassis 24 is mounted in the housing 12, the drive chassis 24 is biased with respect to the housing 12 via the drive spring 74. The drive chassis 24 is further fixed with respect to the housing 12 and a movement relative to the housing 12 in the storage state of the autoinjector 10 via the trigger arm 36 that is held at the opening 138.

In the storage state of the autoinjector 10, the drive spring 74 biases the trigger arm 36 in the axial direction A against the stop feature 54. The trigger arm 36 is present at the right hand side in the opening 138 (of the present Figure).

In order to activate the autoinjector 10 and to release the drive chassis 24 for its proximal movement, the autoinjector 10 comprises the release mechanism 40.

The release mechanism permits relative movement between the needle guard 18 and the drive chassis 24. This relative movement is achieved by an axial movement of the needle guard 18 towards the drive chassis 24 which releases the fixing of the drive chassis 24 with respect to the housing 12 on activation of the autoinjector 10.

For this purpose the plunger arm 142 is configured to cooperate with the trigger arm 36 of the drive chassis 24 for activation of the release mechanism 40. Upon moving the plunger arm 142 in the distal direction the plunger arm 142 contacts and thereby deflects the trigger arm 36 in the transverse direction T as indicated by the arrow B and a comparison of the position of the trigger arm 36 relative to the opening 138 shown in FIGS. 8A to 8C.

The plunger arm 142 of the needle guard 18 comprises a blocking rib 144. The blocking rib 144 is configured to block a radial movement of the trigger arm 36 when the plunger arm 142 contacts the trigger arm 36.

In this connection it should be noted that the blocking rib 144 is also configured to block a radial movement of the trigger arm 36 during the storage state prior to the plunger arm 142 contacting the trigger arm 36 due to an axial movement of the needle guard 18.

In order to engage the trigger arm 36, the plunger arm 142 comprises a cam 162. The cam 162 has an engagement surface 146 configured to engage the trigger arm 36. The engagement surface 146 projects from the cam 162 of the plunger arm 142 at a position adjacent to the blocking rib 144 in the transverse direction T such that it faces the trigger arm 36.

The trigger arm 36 comprises a web 148. The web 148 extends axially (proximally) below the projection 154 from the trigger arm 36 and provides a contact surface in the transverse direction T facing the cam 162 of the plunger arm 142 for engagement with the cam 142 following axial (distal) movement of the needle guard 18.

On distally moving the needle guard 18, the engagement surface 146 engages the web 148. This means that the web 148 and the engagement surface 146 are provided to further facilitate the contact between the trigger arm 36 and the plunger arm 142.

In one embodiment (not shown), the web 148 can comprise a deflection surface 150 inclined with respect to the trigger arm 36 relative to the axial direction A, i.e. a movement direction of the drive chassis 24.

In this connection it should be noted that the deflection surface 150 can be inclined with respect to the axial direction A at an angle selected in the range of 0 to 40°, especially in the range of 5 to 350 and most preferably in the range 10 to 30°.

The engagement surface 146 is also inclined with respect to a movement direction of the drive chassis 24, i.e. with respect to the axial direction A. The engagement surface 146 is inclined to gradually deflect the trigger arm 36 in the direction transverse to the axial direction A of movement of the needle guard 18 in order to shift the trigger arm 36 from the right hand side of the opening 138 of FIG. 8A to the left hand side of the opening 138 of FIG. 8C.

In this connection it should be noted that the engagement surface 146 can be inclined with respect to the trigger arm 36 at an angle selected in the range of 5 to 50°, especially in the range of 7 to 30° and most preferably in the range 8 to 20°.

In this connection it should be noted that the engagement surface 146 and the web 148 are arranged to face one another in a cooperating manner.

When the engagement surface 146 contacts the web 148 respectively the deflection surface 150, the trigger arm 36 is configured to be moved, in particular disengaged, from the stop feature 54, through a deflection in the direction of the arrow B.

The opening 138 at which the stop feature 54 is arranged comprises a surface 152 that has a convex shape. The trigger arm 36 is configured to cooperate with the convex surface 152 of the stop feature 54.

For this purpose the trigger arm 36 comprises a projection 154 engaging the stop feature 54. The projection 154 is configured to cooperate with the opening 138 by engaging into this and by resting on the surface 152 of the stop feature 54 at least in the storage state of the autoinjector 10.

The web 148 is arranged at a surface of the trigger arm 36 different from a surface at which the projection 154 of the trigger arm 36 is arranged. The projection 154 is arranged to project radially from the trigger arm 36, whereas the web 148 is arranged to project transversely from the trigger arm 36.

FIG. 8C shows a state in which the engagement surface 146 of the blocking rib 144 of the plunger arm 142 has moved distally in the axial direction A beyond the axial position of the projection 154, the trigger arm 36 has been deflected in the transverse direction T towards the left hand side of the opening 138 and also radially inwardly in the radial direction R and out of engagement with the stop feature 54.

FIG. 8C shows the state in which the needle guard 18 has been moved distally with respect to the previous figures, i.e. the autoinjector 10 is illustrated in the dispensing state just before the drive spring 74 urges the drive chassis 24 proximally in the axial direction A, as the trigger arm 36 has been released from engagement with the stop feature 54.

Figure 9A:
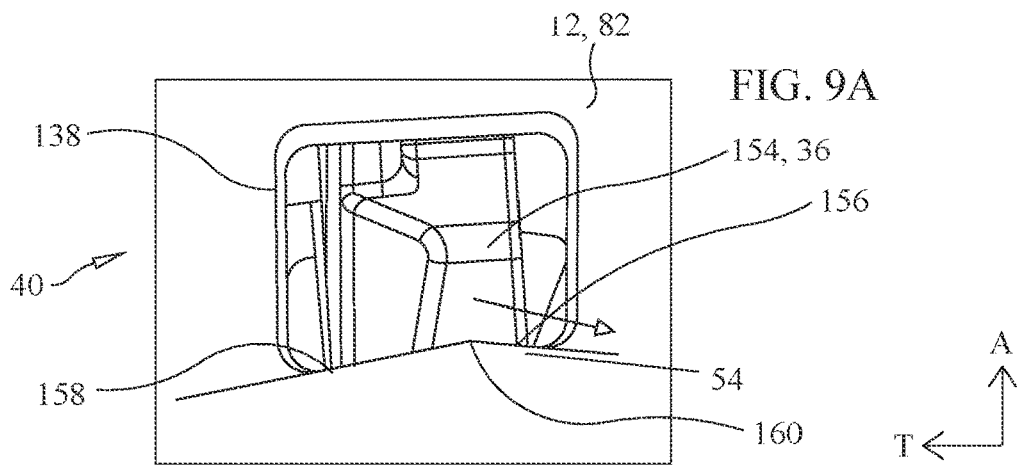
FIGS. 9A to 9C are respective front, side and top views of the release mechanism of FIGS. 8A to 8C.

FIG. 9A shows a front view of the opening 138 of FIG. 8B where the projection 154 is arranged at an apex 160 of the surface 152.

As discussed in the foregoing, the stop feature 54 comprises the convex surface 152 formed by first and second planar surfaces 156, 158 inclined with respect to one another. The first and second planar surfaces 156, 158 adjoin one another at the apex 160 formed therebetween.

In this connection it should be noted that an angle of inclination between the first and second planar surfaces 156, 158 is selected in the range of 110 to 175°, preferably in the range of 120 to 170° and especially in the range of 130 to 165°.

In this connection it should further be noted that an angle between the first planar surface 156 and the axial direction A is selected in the range of 0 to 50°, especially in the range of 1 to 30° and most preferably in the range of 2 to 20°.

In this connection it should further be noted that an angle between the second planar surface 158 and the axial direction A is selected in the range of −20 to 20°, especially in the range of −10 to 10° and most preferably in the range of −5 to 5°.

The apex 160 forms an overhauling angle the trigger arm 36 faces on activation of the autoinjector 10 in order to shift this from the storage state into the dispensing state.

In this connection it should be noted that the faces of the trigger arm can preferably be inclined and angled in such a way that the inclination and angle matches the angles and inclinations of the first and second planar surfaces 156, 158. In this way a contact area between the first and second planar surfaces 156, 158 can be maximised providing an improved attachment between the respective surfaces particularly in the storage state.

Figure 9B:
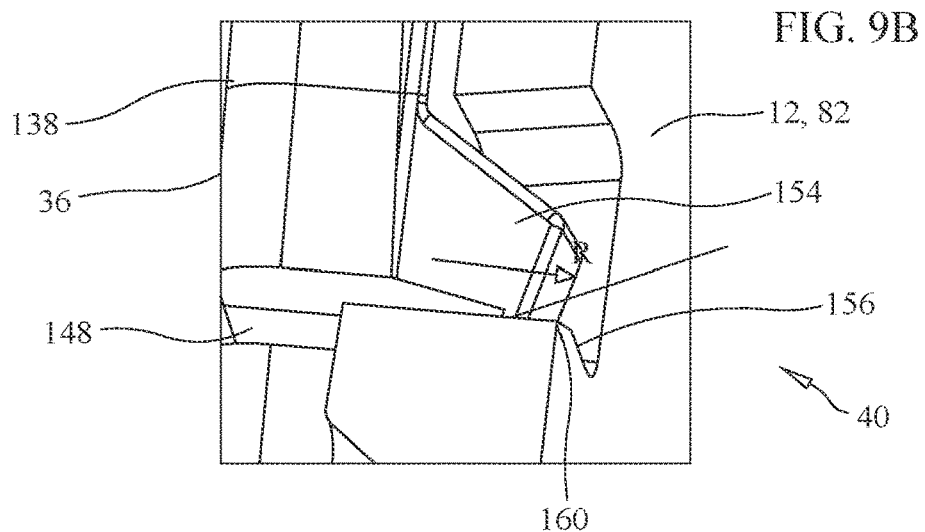
Figure 9C:
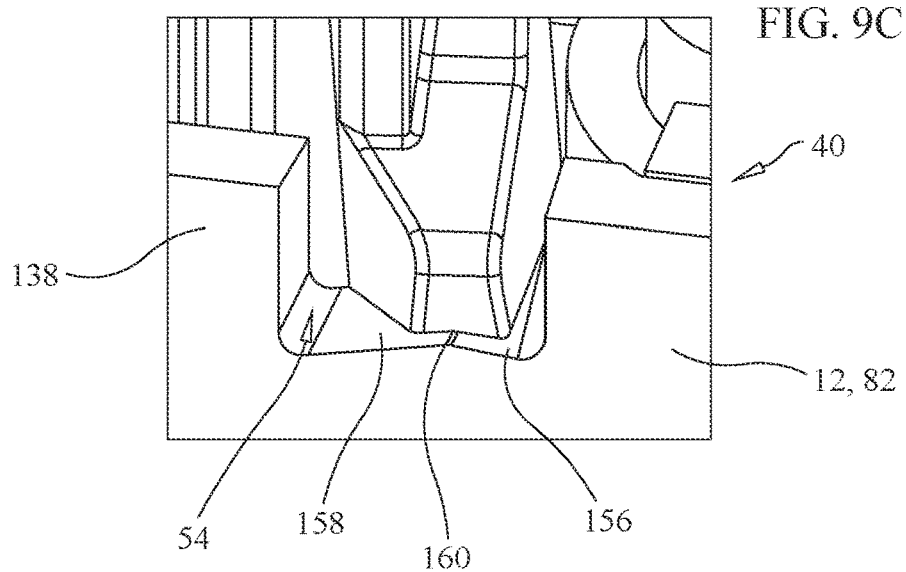

FIG. 9A shows a first view of the release mechanism 40 having the trigger arm 36 of FIGS. 8A to 8C cooperating with the stop feature 54. FIG. 9B shows a second view of the release mechanism 40 and especially the cooperation of the trigger arm 36 with the stop feature 54 in a view perpendicular to that shown in FIG. 9A.

In the storage state the blocking rib 144 is configured to block a radial movement of the trigger arm 36, as it forms a wall against which the trigger arm 36 abuts in the event that the trigger arm 36 is urged radially inwardly in a non-permitted manner, e.g. from the outside of the opening 138 when the plunger arm 142 contacts the trigger arm 36.

In this storage state the drive spring 74 urges the drive chassis 24 in the axial direction A and the drive chassis 24 is axially held in position at the opening 138 via the protrusion 154 of the trigger arm 36.

More specifically, the protrusion 154 is so to say held in the acute space formed by the first planar surface 156 of the stop feature in the opening, as to move the trigger arm 36, this not only has to be moved in the transverse direction T but also distally in the axial direction A.

Once the needle guard 18 is moved towards the drive chassis 24 upon moving the autoinjector 10 from the storage state into the dispensing state, the plunger arm 142 via the engagement surface deflects the trigger arm 36, i.e. via the deflection surface 150 of the web 148, both distally in the axial direction A by lifting the web 148 distally in the axial direction A and pushing the web 148 transversely in the transverse direction T.

Once the projection 154 of the trigger arm 36 has passed the apex 160, the spring force of the drive spring 74 causes the drive spring 74 to relax and urge the drive chassis 24 proximally in the axial direction A and the trigger arm 36 out of engagement from the opening 138 as indicated e.g. in FIG. 8C or shown in FIG. 4C.

Moreover, once the engagement surface 146 of the plunger arm has deflected the trigger arm 36 in the transverse direction T this can also be deflected radially inwardly in the radial direction R. As is shown in FIG. 4B, this is because the transverse deflection of the trigger arm 36 by the engagement surface 146, moves the trigger arm 36 out of possible engagement from the blocking rib 144 of the plunger arm 142, so that the trigger arm can then also deflect radially inwardly in the radial direction R past the blocking rib 144.

Prior to dispensing, the trigger arm 36 of the drive chassis 24 is biased into engagement with the axial stop feature 54 in the outer body 82 of the housing 12.

Under the action of the axial force from the drive spring 74 on the drive chassis 24, the trigger arm 36 is discouraged from moving either transversely or radially inwards by:
- the negative inclined contact surface 156 of the outer body 82 of the housing 12,
- friction acting against them,
- the angle of the trigger arm 36, and
- the stiffness of the trigger arm 36.

In this connection it should be noted that this geometry may require the drive chassis 24 to be slightly lifted and therefore the drive spring 74 to be slightly compressed in order to disengage the trigger arm 36. However, sufficient robustness (i.e. protection against accidental triggering) can be achieved purely by a combination of the load and frictional coefficient of the surfaces of the stop feature 54 and of the trigger arm 36 in contact. If the frictional coefficient is high enough, even a negatively inclined holding surface (opposite to that shown in the diagram) can be functional.

The blocking rib 144 on the needle guard 18 also prevents the trigger arm 36 from moving radially inwards. It would also be feasible to add further blocking rib features (not shown) to the needle guard to prevent transverse movement of the trigger arm 36. These transverse blocking rib features would be arranged such that, during the initial displacement of the needle guard 18 on actuation, they axially disengage from and release transverse movement of the trigger arm 36.

FIG. 8A shows the storage position of the release mechanism 40 in the storage state. The dispensing process is triggered by pressing the needle guard 18 against the user's skin so that it is displaced distally relative to the outer body 82 of the housing 12.

The angled engagement surface 146 of the cam 162 of the needle guard 18 contacts the trigger arm 36 and translates its projection 154 transversely over the apex 160 of the stop feature 54 in the outer body 82 of the housing 12.

Once the projection 154 of the trigger arm 36 is over the apex 160 of the stop feature 54, it engages a steeper slope of the second planar surface 158 that, under the action of the drive spring 74, causes the trigger arm 36 to continue to deflect and eventually disengage the stop feature 54 also in the radial direction without further contact from the needle guard 18.

FIG. 8B shows the release mechanism 40 at the point of triggering, in one optional embodiment, after a short transverse movement, the trigger arm 36 contacts the outer body 82 with a further angled face that forces it to move radially inwards until they disengage entirely from the stop feature 54.

In an alternative embodiment, the cross-section profile of the trigger arm 36 tends to create a radial movement of the projection 154 (to enable disengagement) when the arm 36 is moved transversely.

Once fully disengaged, the drive chassis 24 advances towards the pre-filled syringe 16 to engage the plunger 26 and starts to dispense medicament M under the action of the drive spring 74.

FIG. 8C shows the released position of the release mechanism 40. The overhauling convex surface 152 of the stop feature 54 of the outer body 82 of the housing 12 and the radial lead-in of the trigger arm 36 increases the axial load bearing contact area (which in turn minimises stress for a given drive spring 74 force) while simultaneously requiring only a short travel to trigger. This short travel to trigger tends to reduce the triggering force input required of the user, with the drive spring 74 actually contributing a large part of the triggering energy.

Figures 10A, 10B:
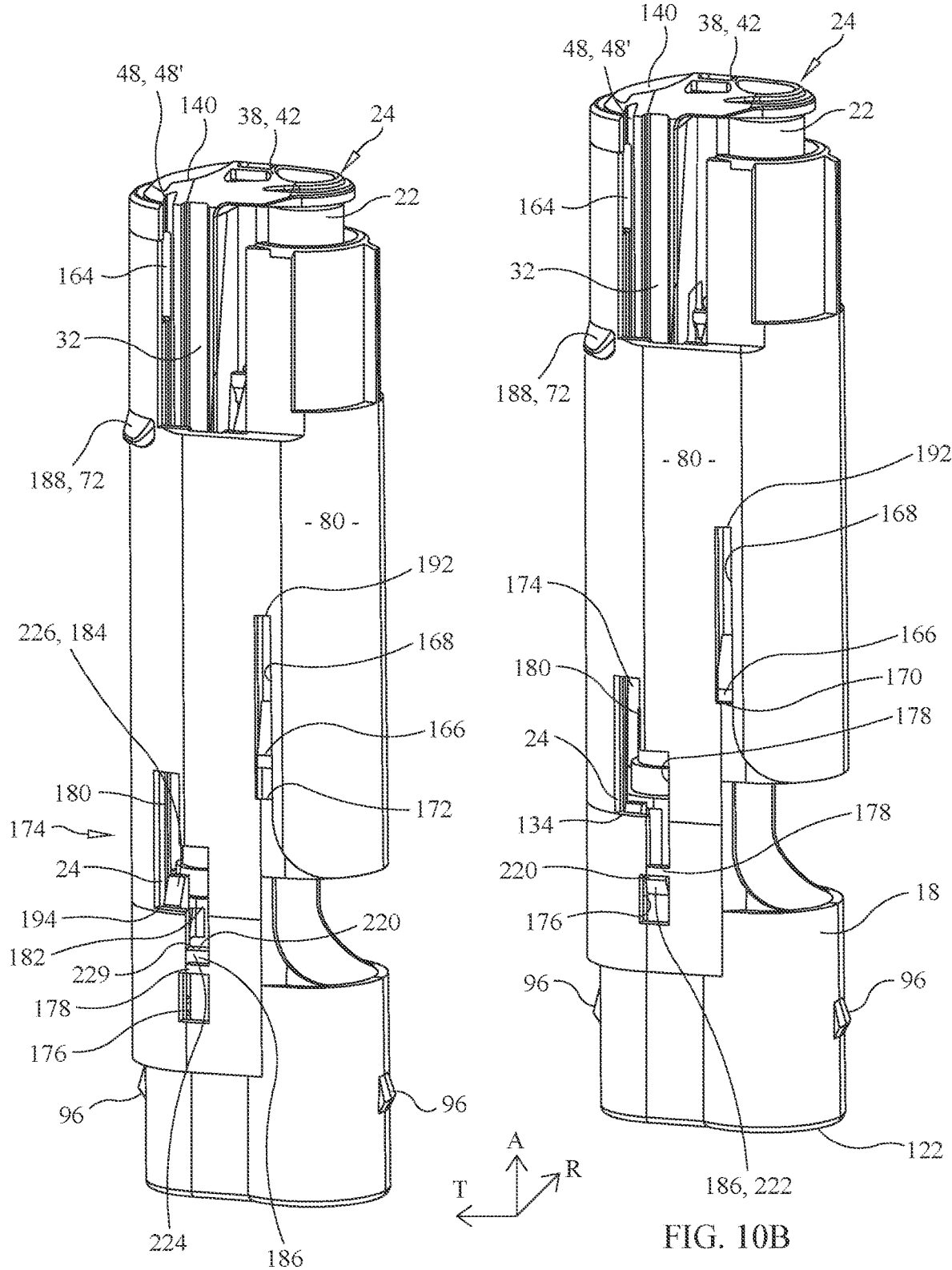
FIG. 10A is a view of the position of a needle guard of the autoinjector relative to the housing in the storage state and FIG. 10B is a view of the position of the needle guard of the autoinjector relative to the housing in the lock-out state.

FIG. 10A shows a view of the position of the needle guard 18 of the autoinjector 10 relative to the inner body 80 of the housing 12 in the storage state of the autoinjector 10. FIG. 10B shows a view of the position of the needle guard 18 of the autoinjector 10 relative to the housing 12 in the lock-out state.

The drive chassis 24 is likewise inserted into the inner body 80. The inner body 80 comprises the lug 164 cooperating with the second groove 48' of the drive chassis 24 as the second guiding aid 48 that enables a linear guidance of the drive chassis 24 within the inner body 80 of the housing 12.

The needle guard 18 comprises a protrusion 166 cooperating with an elongate hole 168 present in the inner body 80, to ensure a linear guidance of the needle guard 18 relative to the inner body 80.

The needle guard 18 further comprises an anti-pull off feature 170. The anti-pull off feature 170 being configured to prevent a removal of the needle guard from the proximal end of the housing 12.

For this purpose the elongate hole 168 comprises a proximal stop 172 that prevents the protrusion 166 from being moved proximally beyond the stop 172 and hence the stop 172 acts as the anti-pull off feature 170 of the needle guard 18.

In this connection it should be noted that the elongate hole 168 is dimensioned such that it is complementary to the shape of the protrusion 166 and such that it defines a linear movement range of the needle guard 16 relative to the inner body 80.

This means that a width of the elongate hole 168 perpendicular to the axial direction A can be selected such that it is complementary to a width of the protrusion perpendicular to the axial direction A.

Moreover, a length of the elongate hole 168 between the proximal stop 172 and a distal stop 192 in parallel with the axial direction A can be selected to correspond to a movement range along the axial direction of the needle guard 18.

The inner body 80 further comprises a first cut-out 174. The first cut-out 174 being configured to cooperate with a clip arm 184 and a lock-out arm 186 of the needle guard 18.

Specifically as shown in FIG. 10A, the clip arm 184 cooperates with a first portion 180 of the first-cut-out 174 and the lock-out arm 186 is configured to cooperate with a second portion 182 of the first cut-out 174.

The first and second portions 180 and 182 of the first cut-out respectively have a rectangular shape, directly adjoin one another and are offset along the axial direction A with respect to one another.

The inner body 80 further comprises a second cut-out 176 that is axially arranged adjacent to the first cut-out 174 and is separated from the first cut-out 174 by a bar 178. The second-cut-out 176 is configured to cooperate with the lock out arm 186.

In this connection it should be noted that the second cut-out is configured to only cooperate with the lock-out arm 186 and thus not with the clip arm 184. This is made possible due to the offset between the first and second portions 180, 182.

In this connection it should further be noted that the lock-out arm comprises an engagement portion 220 that is configured to engage a corresponding cut-out 176.

In the embodiment shown the engagement portion 220 has a ramp 222 via which it can overcome the bar 178 on being moved proximally from the first cut-out 174 to the second cut-out 176 and a planar portion 224 that is configured to drop into the second cut-out 176 and then to act as an abutment that prevents a distal movement of the needle guard 18 out of the lock-out state beyond the bar 178.

As indicated the first cut-out 174 can be present at the same side of the inner body 80 as the elongate hole 168. The first cut-out 174 can also be present at a side different from the side at which the elongate hole 168 is arranged. It is further possible that two first cut-outs 174 and/or two elongate holes 168 are provided that are then arranged at oppositely disposed sides of the inner body 80 (see e.g. FIGS. 14A to 14J).

As also indicated in FIGS. 10A and 10B, the nose 188 of the connection 72 is present at the inner body 80. The nose 188 cooperates with the window 190 shown e.g. in FIGS. 4A to 4C to form the connection 72.

The function of the needle guard 18 before dispensing is as follows:

The needle guard spring, i.e. the lock-out spring 76 (that is biased against the inner body 80) applies a proximal force to the needle guard 18. The needle guard 18 is axially retained within the inner body 80 by its clip arm 184. The needle guard lock-out arm 186 is in clearance to the inner body to avoid long term creep affecting subsequent lock-out robustness.

As the needle guard 18 is pressed during dispense by the user, the clip arm 184 moves up within the first cut-out 174, more specifically within the first portion 180 of the first cut-out 174, in the inner body 80. Towards the end of the dispense stroke of the drive chassis 24 (but before an end of dose click (see FIGS. 11A and 11B), to avoid the associated losses occurring at the same time and reducing the minimum output force from the drive chassis 24), the drive chassis 24 contacts a chamfer 226 of the clip arm 184 of the needle guard 18 thereby, deflecting and holding the clip arms 184 radially inwards. The chamfer 226 aids in the deflection of the clip arm 184 in the radial direction R.

Once a user removes the needle 34 and thereby the needle guard 18 from the skin, the needle guard 18 extends linearly proximally under the action of the lock-out spring 76. Because the clip arm 184 is deflected radially inwards by the drive chassis 24, it does not engage with an inner body assembly stop feature 194 during this return travel. Instead, the needle guard 18 continues to extend until its lock-out arm 184 engages with the bar 178 of the inner body 80 in an extended position to lock the needle guard 18 from being able to move in the distal direction. The bar 178 separates the first cut-out 174 from the second cut-out and the lock-out arm 184 is moveable within the first-cut out 174 during use and prior to lock-out of the needle guard 18.

Moreover, the protrusion 166 prevents the needle guard 18 from being moved more proximally, in the lock-out state as it engages the proximal end of the elongate hole 168 acting as the anti-pull off feature 170.

FIG. 10B shows the extended position of the needle guard 18 following dispense and the lock-out clip 186 engages the bar 178. In the fully extended position, the lock-out arm 186 of the needle guard 18 engages with the bar 178 of the inner body 80 to provide a mechanical lockout against depression of the needle guard 18, thus protecting the user from the risk of needle stick.

FIG. 11A shows a view of the autoinjector 10 in the dispensing state at end of dose, and FIG. 11 AB shows an enlarged view of part of the autoinjector 10 in the dispensing state at the end of dose.

The trigger limb 32 further comprises at least a first part 56 of an audible end of dose feedback member 58 in the shape of a click arm 56. The first part 56, i.e. the click arm 56, is formed by a nose 60, optionally having a generally triangular outer shape, formed at an end of a tongue 62, projecting from the trigger limb 32.

The tongue 62 projects from the trigger limb 32 in the region of a recess 64 formed in the outer surface 49 of the trigger limb 32. An opening 68 of the recess 64 faces in the radial direction R.

The inner body 80 of the housing 12 further comprises at least a second part 66 of the audible end of dose feedback member 58 (see e.g. FIG. 11B).

The second part 66 of the audible end of dose feedback member 58 comprises a distal surface 196 and a proximal surface 198 surrounding an inner body recess 206.

In this connection it should be noted that the positioning of the respective first and second parts 56, 66 of the audible feedback member 58 could be reversed, i.e. the recess 206 could be provided at the drive chassis 24, whereas the tongue 62 could be provided at the inner body 80. It should also be noted that each one of the drive chassis 24 and the inner body 80 could comprise a respective first and second part 56, 66 of the audible feedback member 58 which cooperate with a respective other one of the first and second part 56, 66 of the audible feedback member 58 provided at the other component, i.e. the inner body 80 has both a recess and a tongue each cooperating with a respective one of a tongue and a recess at the drive chassis 24.

On use of the autoinjector 10, the trigger limb 32 is moved by the drive spring 74 in the axial direction A during dispensing, the first part 56 of the audible end of dose feedback member 58 is then deflected in the transverse direction T towards the drive spring 74.

This is achieved as an inclined surface 200 of the end of dose feedback member 58 is deflected by a distal inner housing end 204 of the inner housing 80. This can be aided as the distal inner housing end 204 can be chamfered towards the distal wall 84 of the housing 12.

The audible end of dose feedback member 58 is configured to emit a sound once the material has been dispensed from the autoinjector, i.e. once a click surface 202 of the nose 60 attached to the latching tongue 62 engages the distal surface 196 of the inner body recess 206 by moving in the transverse direction T outwardly The positions of the first and second parts 56, 66 of the audible feedback member 58 are selected such that the audible click occurs once the plunger 26 reaches or is about to reach its final position in the pre-filled syringe 16.

Thereby the audible end of dose feedback member 58 is configured to emit a sound between the drive chassis 24 and the housing 12 once the material has been dispensed from the autoinjector 10.

Thus, towards the end of dose, the nose 60 of the drive chassis 24 engages with a ramp of the inner body 80, i.e. the chamfered distal inner housing end 204 which deflects the tongue 62 radially inwards. Near the end of travel, nose 60 drops through the inner housing recess 206 in the inner body 80, rapidly releasing its deformation and creating an audible click (either by virtue of contact with another component surface or purely acceleration in the air).

FIGS. 12A to 12F show various views of an example of the cap 70 of the autoinjector 10.

Figure 12A:
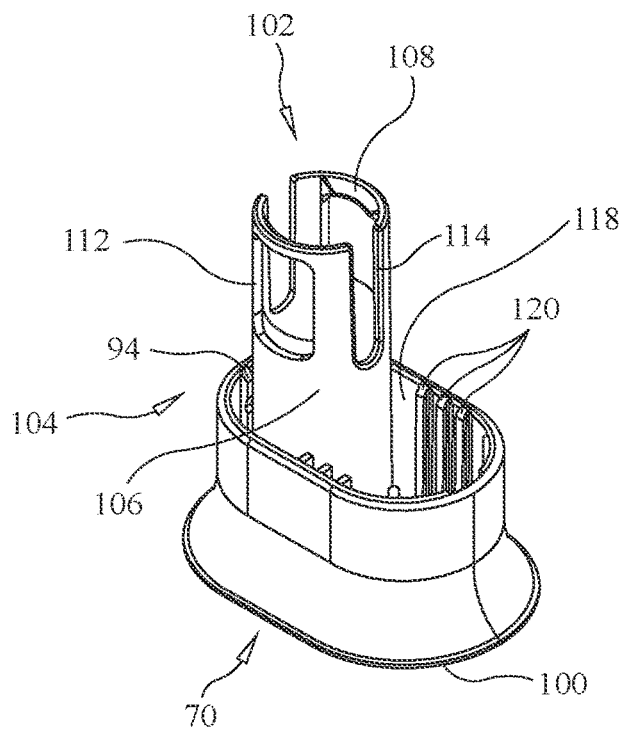

FIG. 12A shows a perspective view of the removable cap 70. The cap 70 is of single piece design. The needle guard 18 is configured to cooperate with the cap 70 via one or more snap-fit connections 94.

Figure 12B:
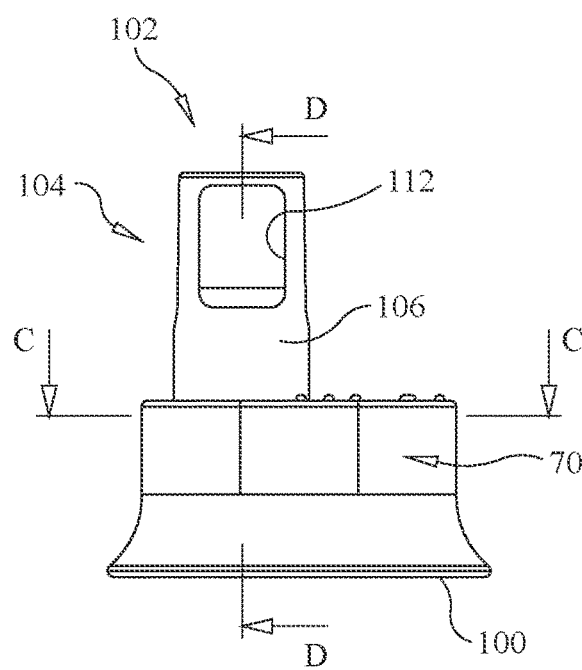
Figure 12C:
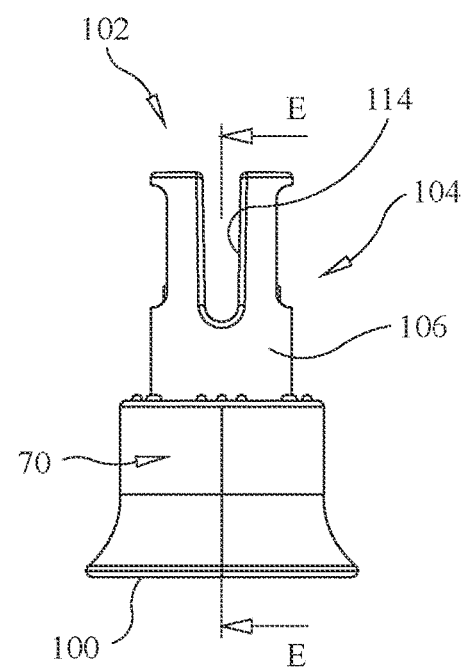

FIGS. 12B and 12C show respective side views of the cap indicating sectional lines C:C, D:D and E:E of the respective sections shown in FIGS. 12D to 12F.

The windows 112 shown in FIG. 12B have an at least generally rectangular shape with rounded edges.

The recesses 114 shown in the FIG. 12C have the shape of a slot with a rounded end and separate the windows 112.

In this connection it should further be noted that the provision of the windows 112 at the needle shield holder 104 also provide a respective tooling lead-in surface that enables ejection of the cap 70 from the injection mold tool.

FIG. 12D shows a section through the cap 70 taken along the sectional line C:C of FIG. 12B. The ribs 120 are provided at the inner surface 118 of the cap 70 only in a region where the needle shield holder 104 is not present within the cap 70.

As indicated in the section shown in FIG. 12E taken along the sectional line D:D of FIG. 12B. The space provided within the needle shield holder 104 for receiving and holding the removable needle shield 78 covering the needle of the pre-filled syringe 16 in the storage state of the autoinjector 10 is visible.

An inner shape of the needle shield holder 104 is shaped complementary to an outer shape of the removable needle shield 78 to aid an as compact a design as possible of the cap 70 and to permit a reliable removal of the removable needle shield 78 on removing the cap 70 from the autoinjector 10.

Moreover, the opening 124 of the cap 70 is formed between the outer wall 116 of the cap 70 and the needle shield holder 104. The dimensions of the opening are selected in dependence on the dimensions of the part of the needle guard that is to be inserted into the opening in the storage state to the autoinjector 10.

The needle shield holder 104 projects distally from the base 100 of the cap 70 and is surrounded by the outer wall 116 of the cap 70. The inner surface 118 of the outer wall 116 of the cap 70 comprises several ribs 120. These ribs are configured to press against the front end 122 of the needle guard 18 when this is arranged within the opening 124.

As indicated in the section shown in FIG. 12F taken along the sectional line E:E of FIG. 12C, the ribs 120 project inwardly into the opening 124 of the cap 70. The ribs 120 are distributed over the inner surface 118 in order to hold the front end 122 of the needle guard 18.

The inner wall 106 of the needle shield holder 104 further comprises the two windows 112, with a respective one of the inwardly facing projections 108 being arranged at each of the windows 112.

Two recesses 114 are formed in the inner wall 106 of the needle shield holder 104 of the cap 70. The recesses are arranged between respective parts of the needle shield holder 104 having the windows 112.

The snap-fit areas 98 of the cap 70 are provided at the inner surface 118 of the cap 70 and a first snap-fit area 208 is formed within some of the ribs 120 of the cap, whereas a second snap in area 210 is formed in a region of the cap 70 free of ribs 120.

The cap 70 is of single piece design and an end face in a proximal surface of the cap 70 at the base 100 does not comprise a hole.

Figure 13A:
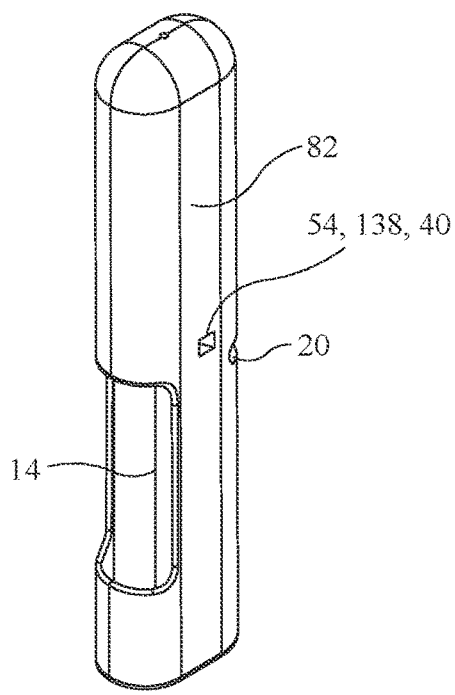
Figure 13B:
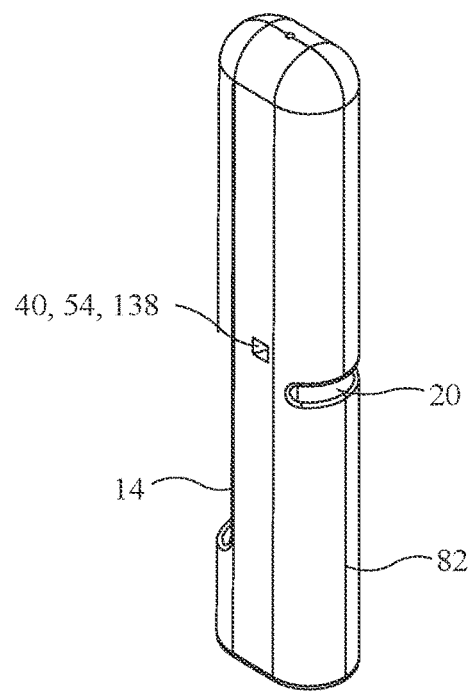
Figure 13C:
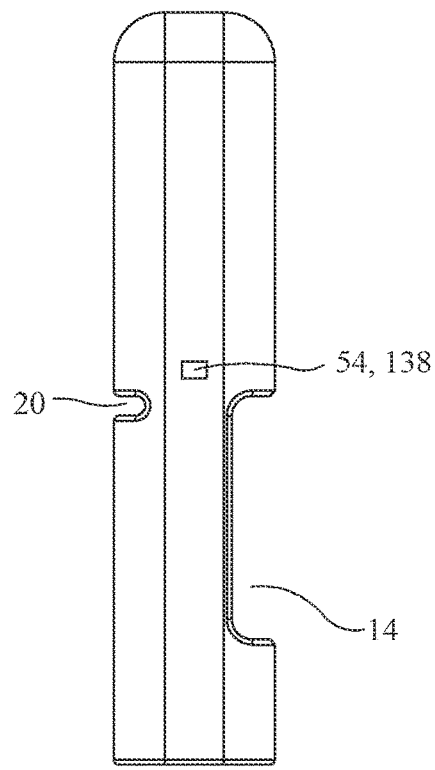
Figure 13D:
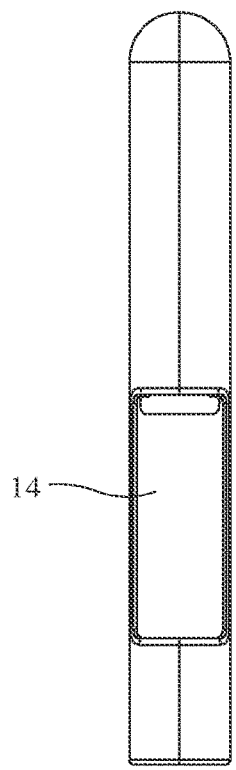
Figure 13E:
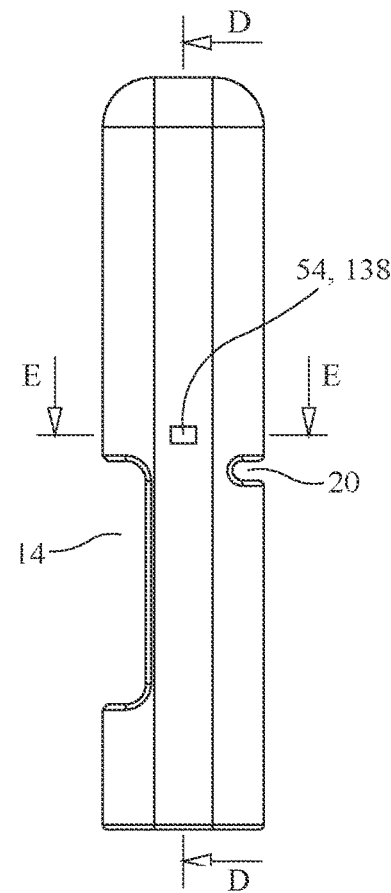

FIGS. 13A to 13J show various views of an example of the outer body 82 of the autoinjector 10. FIGS. 13A and 13B show respective perspective views from two sides of the outer body 82, whereas FIGS. 13C to 13F show respective side views of the outer body 82, FIG. 13G shows a section taken along the sectional line C:C of FIG. 13F, FIG. 13H shows a section taken along the sectional line D:D of FIG. 13E, and FIG. 13I shows a top view of the outer body 82.

FIG. 13J shows a section taken along the sectional line E:E of FIG. 13E. The lug 228 configured to engage the second groove 48' forming the second guiding aid 48 is visible the inner surface 132 of the outer body 82.

In contrast to the embodiment shown in connection with the previous figures, the outer body 82 comprises two stop features 54 present at either side of the outer body 82 in the respective windows 40 as indicated in FIGS. 13A, 13C and 13E.

Moreover, the projection 86 projecting from the distal wall 84 of the outer body 82 of the housing 12 is visible in FIG. 13G. It is arranged at the same transverse position as the trigger limb 32 of the drive chassis 24, as it is intended to be inserted into the passage 140 of the drive chassis 24 on assembly of the autoinjector 10.

In this connection it should be noted that the drive chassis 24 is a component that can be configured to move in a straight line within the housing 12 in order to drive the medicament M stored in the pre-filled syringe 16 arranged within the housing 12 out of the pre-filled syringe 16 on activation of the autoinjector 10 by entraining the plunger 26 of the pre-filled syringe 26.

FIGS. 14A to 14J show various views of an example of the inner body 80 of the autoinjector 10. FIGS. 14A and 14B show respective perspective views from two sides of the inner body 80. The distal housing end 204 having the recess formed thereat are shown at the top of FIGS. 14 and 14b.

FIGS. 14C to 14F show respective side views of the inner body 80, FIG. 14G shows a section taken along the sectional line F:F of FIG. 14E, FIG. 14H shows a section taken along the sectional line E:E of FIG. 14F, FIG. 14I shows a top view of the inner body 80 and FIG. 14J shows a section taken along the sectional line G:G of FIG. 14E.

The inner body 80 is configured to cooperate with the outer body 82 of FIG. 13 and with the needle guard 18 shown in the following in FIGS. 15A to 15J. The inner body 80 has two first cut-outs 174, two second cut-outs 176 and two elongate holes 168 arranged at oppositely disposed sides of the inner body 80 and configured to engage corresponding parts of the needle guard 18.

FIGS. 15A to 15J show various views of an example of the needle guard 18 of the autoinjector 10, it is configured to cooperate with the inner body 80 of FIGS. 14A to 14J, for this purpose it includes two protrusions 166 cooperating with a respective one of the elongate holes 168, two lock-out arms 186 cooperating with a respective one of the first and second cut-outs 174, 176 separated by a respective bar 178, and two respective clip-arms 184 engaging the respective first cut-outs 174 and the trigger limb 32 of the drive chassis 24.

Moreover, the needle guard 18 also comprises a single plunger arm 142 having two blocking ribs 144 and two cams shaped in the manner described in the foregoing. The blocking ribs 144 are configured to cooperate with the drive chassis 24 discussed in connection with FIGS. 17A to 17L when inserted into the housing 12 comprising the outer body 82 discussed in connection with FIGS. 13C to 13J and the inner body 80 discussed in connection with FIGS. 14A to 14J. It should also be noted that the blocking ribs 144 are arranged at opposite sides of the plunger arm 142.

Figure 15F:
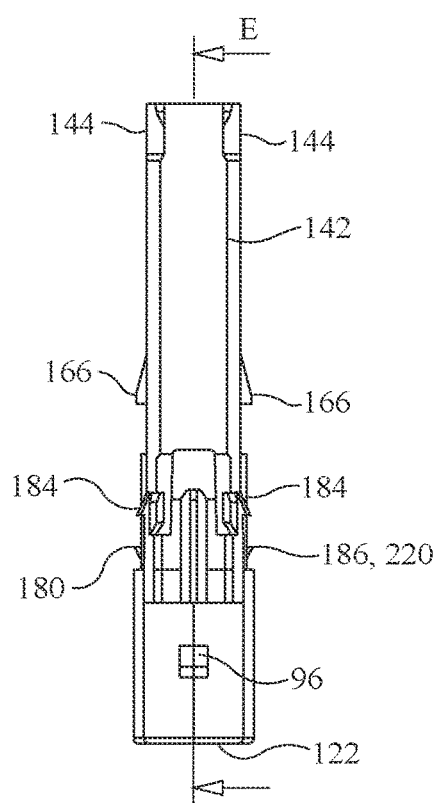
Figure 15G:
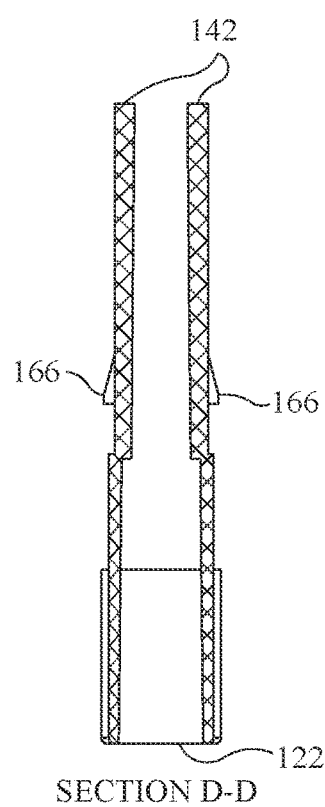
Figure 15H:
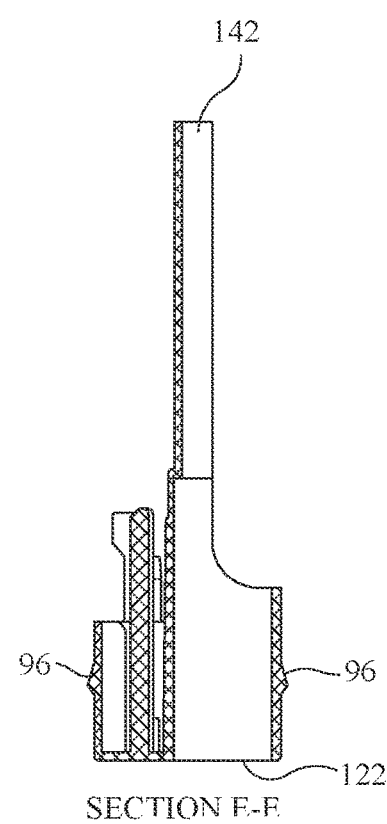
Figure 15I:
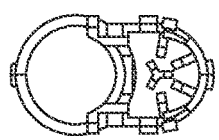
Figure 15J:
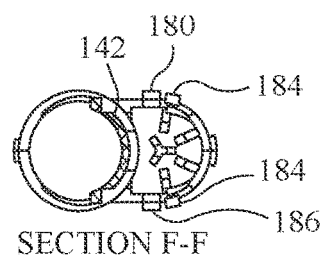

FIGS. 15A and 15B show respective perspective views from two sides of needle guard 18, whereas FIGS. 15C and 15F show respective side views of the needle guard 18, FIG. 15G shows a section taken along the sectional line D:D of FIG. 15E, FIG. 15H shows a section taken along the sectional line E:E of FIG. 15F, FIG. 15I shows a top view of the needle guard 18 80 and FIG. 15J shows a section taken along the sectional line F:F of FIG. 15E.

FIGS. 16A to 16K show various views of an example of the needle shield 78 of the autoinjector 10. The needle shield 78 has a needle receptacle 212 at an end thereof comprising the syringe facing surface 110. The syringe facing surface 110 is arranged opposite to a front end 214 of the needle shield 78. The needle shield 78 has outer dimensions configured to be received in the needle shield holder 104 and inner dimensions adapted to receive the needle 34 of the pre-filled syringe 16.

Figure 16A:
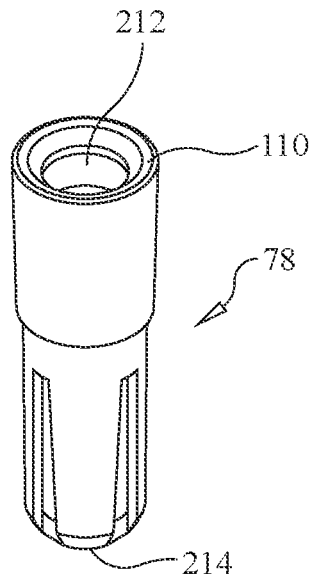
Figure 16B:
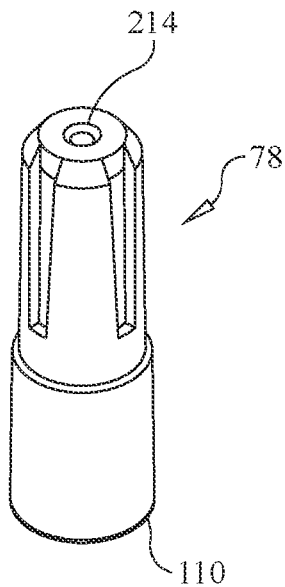
Figure 16C:
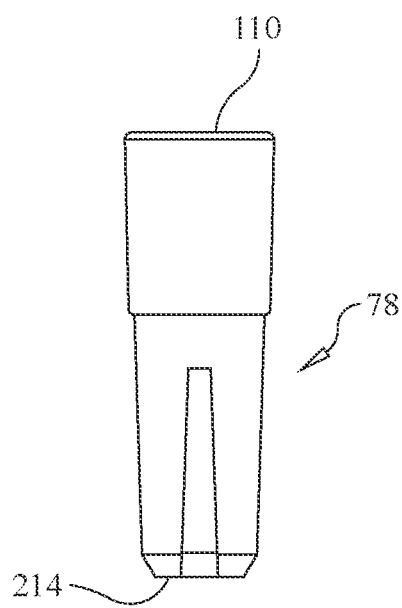
Figure 16D:
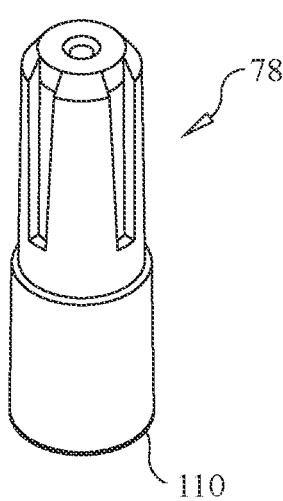
Figure 16E:
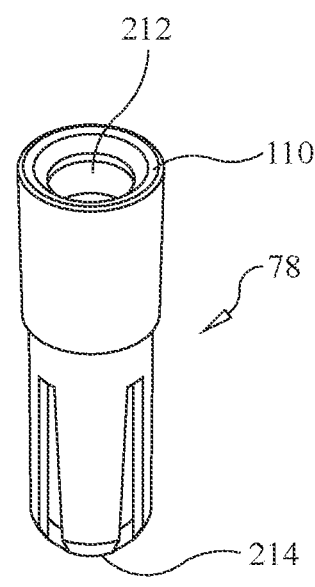

FIGS. 16A, 16B, 16F and 16E show various perspective views from above and below of the needle shield 78, FIGS. 16C, 16F, 16G and 16H respective side views of the needle shield 78, FIG. 16I shows a section taken along the sectional line B:B of FIGS. 16G and 16J shows a view from the front end 214 and FIG. 16K shows a section taken along the sectional line C:C of FIG. 16G.

The section B:B of FIG. 16I indicates that the needle receptacle 212 is shaped complementary to the needle 34 of the pre-filled syringe 16. The function of the needle shield 78 is to protect the needle 34 from external influences.

FIGS. 17A to 17L show various views of an example of the drive chassis 24 of the autoinjector 10. The drive chassis 24 has two trigger arms 36 each with its respective components as discussed in the foregoing, a single audible feedback member 58 arranged at a side of the drive chassis 24.

Figure 17G:
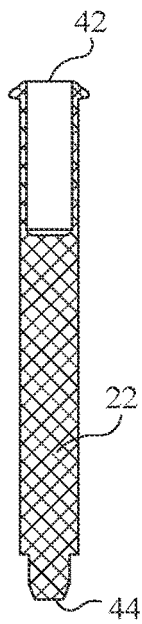

FIGS. 17A, 17B show perspective views of the drive chassis 24, whereas FIGS. 17C to 17F show different side views of the drive chassis 24. FIG. 17G shows a section taken along the section line E:E of FIG. 17E through the dispensing limb 22 having the plunger support 44.

Figure 17H:
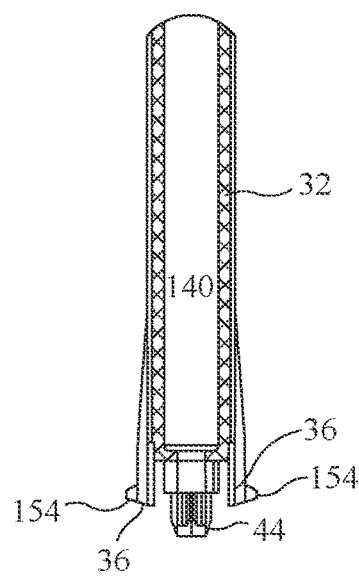

FIG. 17H, shows a section taken along the sectional line F:F of FIG. 17E through the trigger limb 32 indicating the passage 140 formed therein.

Figure 17I:
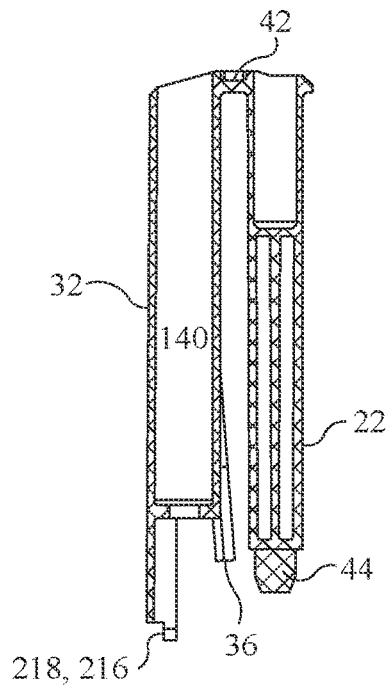

FIG. 17I shows a section taken along the sectional line G:G of FIG. 17F showing the parallel arrangement of the dispensing limb 22 and the trigger limb 32.

Figure 17J:
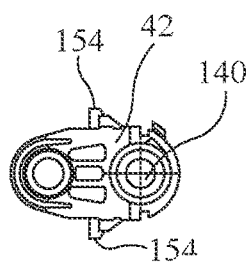

FIG. 17J shows a top view of the drive chassis 24 with the projections 154 of the trigger arms 36 projecting radially outwardly from the drive chassis 24.

Figure 17K:
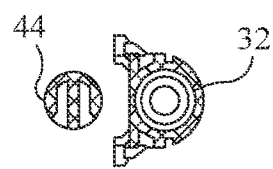
Figure 17L:
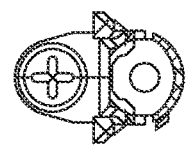

FIG. 17K shows a section taken along the sectional line D:D of FIG. 17E and FIG. 17L shows a section taken along the sectional line C:C of FIG. 17E at a height of the drive chassis 24 where the two projections 154 are positioned relative to the trigger arms 36.

FIG. 17D and f by way of example show that the trigger limb 32 comprises a lip 216 at an end disposed opposite to the web 42. The lip 216 is configured to engage the clip arms 184 formed at the needle guard 18.

The lip 216 comprises two tips 218, with each tip 218 being configured to engage a respective one of the clip arms 184 formed at the needle guard 18.

It should also be noted that the first and second guiding aids extend proximally from the web 42, with the second groove 48' extending directly from the web 42 and the first groove 46' begin offset from the web 42.

In the foregoing the mechanism elements of a disposable auto-injector 10 to dispense medicament M from the pre-filled syringe (PFS) 16 are described. The design disclosed permits state of the art features to be incorporated into a small physical package using a very small number of low cost components and a very simple process, compared to the state of the art.

The auto-injector device disclosed includes an assembly surrounding a pre-filled syringe (PFS) 16 that contains medicament M. Typically, such devices are single-use and intended for administration by a patient (i.e. self-administration) or carer.

At point of use, the user removes the protective Cap 70 from the proximal end of the autoinjector 10, positions the autoinjector 10 at the injection site (typically the skin of the thigh or belly) and presses the autoinjector 10 axially in a proximal direction, to achieve needle insertion of the needle 34 into the skin and to initiate dispense.

Energy from a helical compression drive spring 74 is released to displace the plunger 26 within the PFS 16 and deliver the medicament M to the patient. An audible click notifies the patient that dispense has started. In this connection it should be noted that such an audible click can be generated when the trigger arm 36 cooperates with the stop feature 54 on triggering the release mechanism 40 upon moving the autoinjector 10 from the storage state to the dispensing state. The progress of dispense can be monitored by the user as a change in position of the PFS plunger 26 and mechanism plunger within the large wrap-around 'syringe window' 14.

The user is notified when the dose is complete by an audible click emitted from the autoinjector 10 and a change in the colour displayed within a unique 'status indicator window' 20. The autoinjector 10 can then be removed from the injection site, allowing the sprung needle guard 18 to extend to a locked position under the action of a separate helical compression spring 76 to cover the needle 34. In this locked position, the needle guard 18 covers the needle 34 and protects the patient or a further person from needle 34 stick injuries.

The mechanism described utilises a parallel drive arrangement where the axis of the drive spring 74 is offset from the axis of the PFS 16, rather than passing into the bore of the PFS 16 as is common in the prior art. This arrangement has a number of advantages:

The length of the autoinjector 10 can be minimised so that it is largely determined by the PFS 16 length and plunger 26 travel.

It allows flexibility in the specification of the drive spring 74 (e.g. to increase or reduce the force it applies or make other modifications to improve the efficiency of manufacturing), since its geometry is not constrained by the PFS 16 bore diameter.

It allows improved access to components and features, where a tubular arrangement often necessitates a number of concentric (or at least co-axial) components that move relative to each other, which can then be challenging to connect with each other in the optimal way.

The improved access further allows simpler interactions between components to create features for triggering, feedback and lock-out which tend to avoid the need for additional parts or complex mechanisms.

The simplicity of the mechanism results in a reduced number of components, which in turn helps to minimise the number of wall thicknesses required and hence device width and depth.

Due to the disposable nature of single-use auto-injectors 10, it is considered advantageous to minimise autoinjector 10 complexity, material usage, package size and assembly complexity in this way, as this all tends to reduce cost and environmental impact by:

Reducing the volume of raw materials used,
Reducing the cost of manufacturing equipment and the assembly process,
Reducing the volume required in transport and storage, which can be particularly expensive when low temperatures are required.

The disclosed invention achieves this simplicity and small size whilst incorporating state of the art user features and adding innovative new user features.

Enumerated Embodiments

1. An autoinjector 10 comprising:
    a housing 12,
    a pre-filled syringe 16 mounted in the housing 12 and fixed relative to the housing 12, and a needle guard 18 mounted axially moveable in the housing 12 for movement between a storage state, a dispensing state and a lock-out state in which states the needle guard 18 adopts different axial positions relative to the housing 12,
    wherein the needle guard 18 is configured to be axially moved in a distal direction between the storage state and the dispensing state and
    wherein the needle guard 18 is configured to be axially moved in a proximal direction between the dispensing state and the lock-out state.
2. The autoinjector 10 according to embodiment 1, wherein the needle guard 18 surrounds a needle 34 of the pre-filled syringe 16 in the storage state and in the lock-out state.
3. The autoinjector 10 according to embodiment 1 or embodiment 2, wherein the needle guard 18 does not surround a needle 34 of the pre-filled syringe 16 in the dispensing state.
4. The autoinjector 10 according to one of embodiments 1 to 3, further comprising a lock-out spring 76 arranged between the needle guard 18 and the housing 12.
5. The autoinjector 10 according to embodiment 4, wherein the needle guard 18 is configured to compress the lock-out spring 76 upon moving between the storage state and the dispensing state.
6. The autoinjector 10 according to embodiment 4 or embodiment 5, wherein the needle guard 18 is configured to be moved by a relaxation of the lock-out spring 76 between the dispensing state and the lock-out state.
7. The autoinjector 10 according to one of embodiments 1 to 6, wherein the needle guard 18 comprises one or more lock-out arms 186.
8. The autoinjector 10 according to embodiment 7, wherein the one or more lock-out arms 186 comprise an engagement portion 220 that is configured to engage a corresponding cut-out 176 in the housing 12 of the autoinjector 10 in the lock-out state.

9. The autoinjector 10 according to one of embodiments 4 to 8 and embodiment 7, wherein two or more lock-out arms 186 are provided, with the lock-out spring 76 being arranged between the two or more lock-out arms 186.

10. The autoinjector 10 according to one of embodiments 1 to 9, wherein the needle guard 18 comprises an anti-pull off feature 170 cooperating with the housing 12.

11. The autoinjector 10 according to one of embodiments 1 to 10, wherein the needle guard 18 comprises a plunger arm 142 for activation of a release mechanism 40 of the autoinjector 10.

12. The autoinjector 10 according to embodiment 10 and embodiment 11, wherein the anti-pull off feature 170 is arranged at the plunger arm 142.

13. The autoinjector 10 according to one of embodiments 10 to 12, wherein the anti-pull of feature 170 comprises a protrusion 166 that engages a hole 168 present in the housing 12.

14. The autoinjector 10 according to one of embodiments 1 to 13, further comprising a drive chassis 24, the drive chassis 24 being mounted in the housing 12, the drive chassis 24 being biased with respect to the housing 12, the drive chassis 24 further being fixed with respect to the housing 12 and a movement relative to the housing 12 in a storage state of the autoinjector 10.

15. The autoinjector 10 according to embodiment 14 and of embodiments 7 to 13, wherein the drive chassis 24 is configured to engage the one or more clip arms 184 to deflect these radially inwardly away from the housing 12 in the dispensing state.

16. The autoinjector 10 according to embodiment 14 or embodiment 15 and one of embodiments 11 to 13, wherein the plunger arm 142 is configured to cooperate with a trigger arm 36 of the drive chassis 24 for activation of a release mechanism 40 of the autoinjector 10.

17. The autoinjector 10 according to one of embodiments 14 to 16, wherein an axial movement of the needle guard 18 towards the drive chassis 24 releases the fixing of the drive chassis 24 with respect to the housing 12 on activation of the autoinjector 10.

18. The autoinjector 10 according to embodiment 16 or embodiment 17, wherein the axial movement of the needle guard 18 is configured to deflect the trigger arm 36 in a direction transverse to the axial movement.

19. The autoinjector 10 according to one of embodiments 16 to 18 and one of embodiments 11 to 15, wherein the plunger arm 142 is configured to deflect the trigger arm 36 in a direction transverse to the axial movement of the needle guard 18.

20. The autoinjector 10 according to one of embodiments 1 to 19, wherein the needle guard 18 comprises a blocking rib 144.

21. The autoinjector 10 according to embodiment 20 and one of embodiments 16 to 19, wherein the blocking rib 144 is configured to block a radial movement of the trigger arm 36.

22. The autoinjector 10 according to one of embodiments 1 to 21, wherein the needle guard 18 further comprises cam 162 having an engagement surface 146.

23. The autoinjector 10 according to one of embodiments 16 to 21 and embodiment 22, wherein the engagement surface 146 is configured to engage the trigger arm 36.

24. The autoinjector 10 according to embodiment 23, wherein the trigger arm 36 comprises a web 148 and the engagement surface 146 engages the web 148 of the trigger arm 36.

25. The autoinjector 10 according to one of embodiments 21 to 24 and embodiment 20, wherein the engagement surface 146 projects from the blocking rib 144.

26. The autoinjector 10 according to embodiment 24 or embodiment 25, wherein the web 148 comprises a deflection surface 150 inclined with respect to a movement direction of the drive chassis 24.

27. The autoinjector 10 according to one of embodiments 22 to 26, wherein the engagement surface 146 is inclined with respect to a movement direction of the drive chassis 24.

28. The autoinjector 10 according to embodiment 26 and embodiment 27, wherein the engagement surface 146 and the deflection surface 150 are inclined with respect to a movement direction of the drive chassis 24 in a cooperating manner.

29. The autoinjector 10 according to embodiment 28, wherein the engagement surface 146 is inclined to deflect the trigger arm 36 in the direction transverse to the axial direction of movement of the needle guard 18.

30. The autoinjector 10 according to one of embodiments 14 to 29, further comprising a drive spring 74, with the drive spring 74 being configured to drive the drive chassis 24 towards the needle guard 18 after activation of the autoinjector 10.

31. The autoinjector 10 according to one of embodiments 1 to 30, wherein the needle guard 18 is configured to cooperate with a cap 70 via one or more snap-fit connections 94.

32. The autoinjector 10 according to embodiment 31, wherein each snap fit connection comprises a snap-fit projection 96 cooperating with a corresponding snap-fit area 98.

33. The autoinjector 10 according to embodiment 32, wherein the needle guard 18 comprises one or more snap-fit projections 96.

34. The autoinjector 10 according to embodiment 32 or embodiment 33, wherein one or more snap-fit projections 96 are provided at an outer surface 126 of the needle guard 18.

35. The autoinjector 10 according to one of embodiments 32 to 34, wherein an inner surface 128, 132 of the housing 12 comprises one or more grooves 130, 134 in which one or more of the snap-fit projections 96 can axially move relative to the housing 12 upon axial movement of the needle guard 18.

36. The autoinjector 10 according to one of embodiments 31 to 35, wherein a front end 122 of the needle guard 18 is arranged within an opening 124 of the cap 70.

37. The autoinjector 10 according to one of embodiments 31 to 36, wherein an outer wall 116 of the cap 70 contacts an outer wall 136 of the housing 12 in the storage state of the autoinjector 10.

38. The autoinjector 10 according to embodiment 37, wherein the outer wall 116 of the cap 70 and the outer 136 wall of the housing 12 do not overlap in an axial direction of the autoinjector 10.

39. The autoinjector 10 according to embodiment 37 or embodiment 38, wherein the outer wall 116 of the cap 70 and the outer wall 136 of the housing 12 radially overlap in the storage state of the autoinjector 10.

40. The autoinjector 10 according to one of embodiments 1 to 39, wherein the housing 12 is a two-part housing 12 comprising an inner body 80 and an outer body 82.
41. The autoinjector 10 according to one of embodiments 1 to 40, further comprising a drive chassis 24 mounted in the housing 12, the drive chassis 24 being biased with respect to the housing 12, the drive chassis 24 further being fixed with respect to the housing 12 and for a movement relative to the housing 12 in a storage state of the autoinjector 10, the drive chassis 24 moving relative to the housing 12 on dispensing a material from the pre-filled syringe 16.
42. The autoinjector 10 according to embodiment 41, wherein the autoinjector 10 is configured to generate an audible end of dose feedback between the drive chassis 24 and the housing 12 once the material has been dispensed from the autoinjector 10.
43. The autoinjector 10 according to one of embodiments 1 to 42, further comprising a drive chassis 24 mounted in the housing 12, the drive chassis 24 being biased with respect to the housing 12 by a drive spring 74, the drive chassis 24 further being fixed with respect to the housing 12 and a movement relative to the housing 12 in a storage state of the autoinjector 10.
44. The autoinjector 10 according to embodiment 43, wherein the drive chassis 24 comprises a trigger arm 36 engaging a stop feature 54 present in the housing 12 in the storage state of the autoinjector 10 for fixing the drive chassis 24 with respect to the housing 12.
45. The autoinjector 10 according to embodiment 44, wherein the trigger arm 36 is configured to be disengaged from the stop feature 54 on activation of the autoinjector 10.
46. The autoinjector 10 according to one of embodiments 1 to 45, further comprising a needle shield 78 covering a needle 34 of the pre-filled syringe 16 in a storage state of the autoinjector 10, the axially moveable needle guard 18 arranged to cover the needle 34 of the pre-filled syringe 16 at least after use of the autoinjector 10 and to move relative to the pre-filled syringe 16 during use of the autoinjector 10, as well as a removable cap 70 in which the needle guard 18 is stored in the storage state of the autoinjector 10.
47. The autoinjector 10 according to embodiment 46, wherein the cap 70 is removably connected to the needle guard 18 in the storage state of the autoinjector 10, and wherein, on removal of the cap 70, the needle shield 78 is also removed from the autoinjector 10.
48. The autoinjector 10 according to one of embodiments 1 to 47, further comprising a drive chassis 24 mounted in the housing 12, the drive chassis 24 being biased with respect to the housing 12 and being fixed with respect to the housing 12 in a storage state of the autoinjector 10.
49. The autoinjector 10 according to embodiment 48, further comprising a status indicator window 20 arranged at the housing 12 via which the drive chassis 24 is visible from the outside, with the status indicator window 20 showing a first part 50 of the drive chassis 24 in the storage state of the autoinjector 10 and a second part 52 of the drive chassis 24 after use of the autoinjector 10, with the first and second parts 50, 52 of the drive chassis 24 being distinguishable from one another.
50. The autoinjector 10 according to one of embodiments 1 to 49, further comprising a drive chassis 24, the drive chassis 24 comprising a dispensing limb 22 and a trigger limb 32, wherein a plunger 26 is arrangeable at a proximal end of the dispensing limb 22 and a trigger arm 36 is arranged extending proximally from the trigger limb 32.
51. The autoinjector 10 according to embodiment 50, wherein the trigger limb 32 and the dispensing limb 22 are arranged in parallel to one another respectively at least essentially in parallel to one another and are connected to one another at a respective distal end side of the dispensing limb 22 and the trigger limb 32 via a web 42.
52. An autoinjector 10, optionally in accordance with one of embodiments 1 to 51, the autoinjector 10 comprising:
a housing 12,
a pre-filled syringe 16 mounted in the housing 12,
a drive chassis 24 mounted in the housing 12, the drive chassis 24 being biased with respect to the housing 12, the drive chassis 24 further being fixed with respect to the housing 12 and for a movement relative to the housing 12 in a storage state of the autoinjector 10, the drive chassis 24 moving relative to the housing 12 on dispensing a material from the pre-filled syringe 16, and
wherein the autoinjector 10 comprises an audible feedback member 58 is configured to generate an audible end of dose feedback between the drive chassis 24 and the housing 12 once the material has been dispensed from the autoinjector 10.
53. The autoinjector 10 according to one or more of the preceding embodiments, wherein drive chassis 24 comprises a first part 56 of the audible feedback member 58 that engages a second part 66 of the audible feedback member 58 arranged at the housing 12 to generate the audible end of dose feedback.
54. The autoinjector 10 according to one or more of the preceding embodiments, wherein the housing 12 comprises a recess 208 and the drive chassis 24 engages the recess 208 to generate the audible end of dose feedback.
55. The autoinjector 10 according to embodiment 53 and embodiment 54, wherein the first part 56 of the audible feedback member 58 of the drive chassis 24 engages the recess 208 to generate the audible end of dose feedback
56. The autoinjector 10 according to one or more of the preceding embodiments, wherein the housing 12 comprises a chamfered distal inner housing end 204 on an inner surface 132 thereof.
57. The autoinjector 10 according to embodiment 56, wherein the chamfered distal inner housing end 204 deflects a part of the drive chassis 24 radially inwardly as this moves from the storage state to an end of dose state.
58. The autoinjector 10 according to embodiment 57 and one of embodiments 53 to 56, wherein the chamfered distal inner housing end 204 deflects the first part 56 of the audible feedback member 58 radially inwardly as the drive chassis 24 moves from the storage state to an end of dose state.
59. The autoinjector 10 according to embodiment 58, wherein the chamfered distal inner housing end 204 is configured to deflect the first part 56 of the audible feedback member 58 radially inwardly before the first part 56 of the audible feedback member 58 engages the recess 208.

60. The autoinjector 10 according to one or more of the preceding embodiments, wherein the audible end of dose feedback comprises an audible click.
61. The autoinjector 10 according to embodiment 60, wherein the audible click is brought about by at least one of a contact between two components 56, 66 and an acceleration of a component 56.
62. The autoinjector 10 according to embodiment 60 or embodiment 61 and one of embodiments 57 to 59, wherein the audible click is generated by a radially outwardly directed relaxation of the radially inwardly deflected part 56 of the drive chassis 24.
63. The autoinjector 10 according to one or more of the preceding embodiments, wherein the drive chassis 24 further comprises a plunger support 44 for engaging a plunger 26 of the pre-filled syringe 16.
64. The autoinjector 10 according to embodiment 63 and one of embodiments 55 to 62, wherein the first part 56 of the audible feedback member 58 extends from the drive chassis at a part of the drive chassis 24 different from the plunger support 44.
65. The autoinjector 10 according to one or more of the preceding embodiments further comprising a drive spring 74 mounted between the drive chassis 24 and the housing 12.
66. The autoinjector 10 according to embodiment 65 and one of embodiments 63 and 64, wherein a relaxation of the drive spring 74 drives the plunger support 44 towards the plunger 26 of the pre-filled syringe 16 after activation of the autoinjector 10.
67. The autoinjector 10 according to embodiment 66, wherein the drive spring 74 is arranged within a part of the drive chassis 24 comprising the first part 56 of the audible feedback member 58, in particular in a passage 140.
68. The autoinjector 10 according to one or more of the preceding embodiments, wherein the housing 12 is a two-part housing comprising an inner body 80 and an outer body 82.
69. The autoinjector 10 according to embodiment 68, wherein the inner body 80 and the outer body 82 are fixed in position relative to one another.
70. The autoinjector 10 according to embodiment 68 or embodiment 69, wherein the inner body 80 and the outer body 82 are connected to one another via a connection 72.
71. The autoinjector 10 according to embodiment 70, wherein the connection 72 is formed by a nose 188 engaging a window 190.
72. The autoinjector 10 according to embodiment 71, wherein the nose 188 is formed at the inner body 80 and engages the window 190 formed at the outer body 82.
73. The autoinjector 10 according to embodiment 68 and one of embodiments 54 to 72, wherein the inner body 80 comprises the recess 208.
74. The autoinjector 10 according to one or more of the preceding embodiments, wherein the inner body 80 comprises one or more cut-outs 174, 176 and/or holes 168 that are configured to cooperate with one or more corresponding parts 184, 186, 166 of the needle guard 18.
75. The autoinjector 10 according to one or more of the embodiments 68 to 74 and one or more of the embodiments 54 to 66, wherein the drive spring 74 is arranged between the outer body 82 and the drive chassis 24.
76. The autoinjector 10 according to one or more of the preceding embodiments, wherein the drive chassis 24 is of generally U-shaped design and comprises a dispensing limb 22 as well as a trigger limb 32.
77. The autoinjector 10 according to one or more of the preceding embodiments, wherein the drive chassis 24, the first part 56 of the audible feedback member 58 and the plunger support 44 are formed in one piece from the same material.
78. An autoinjector 10, optionally in accordance with one or more of the preceding embodiments, the autoinjector 10 comprising:
a housing 12 in which a pre-filled syringe 16 is arranged,
a drive chassis 24 mounted in the housing 12, the drive chassis 24 being biased with respect to the housing 12 by a drive spring 74, the drive chassis 24 further being fixed with respect to the housing 12 and a movement relative to the housing 12 in a storage state of the autoinjector,
the drive chassis 24 comprising a trigger arm 36 engaging a stop feature 54 present in the housing 12 in the storage state of the autoinjector 10 for fixing the drive chassis 24 with respect to the housing 12, and
wherein the trigger arm 36 is configured to be disengaged from the stop feature 54 on activation of the autoinjector 10.
79. The autoinjector 10 according to one or more of the preceding embodiments, wherein the stop feature 54 comprises an opening 138.
80. The autoinjector 10 according to one or more of the preceding embodiments, wherein the stop feature 54 comprises a convex surface 152.
81. The autoinjector 10 according to embodiment 80, wherein the trigger arm 36 is configured to cooperate with the convex surface 152 of the stop feature 54.
82. The autoinjector 10 according to one or more of the preceding embodiments, wherein the trigger arm 36 comprises a projection 154 engaging the stop feature 54.
83. The autoinjector 10 according to embodiment 82, wherein the projection 154 is configured to cooperate with the opening 138.
84. The autoinjector 10 according to one of embodiments 82 or embodiment 83, wherein the projection 156 is configured to cooperate with the convex surface 152.
85. The autoinjector 10 according to one or more of the preceding embodiments, wherein the trigger arm 36 comprises a web 148 projecting therefrom.
86. The autoinjector 10 according to embodiment 85 and embodiment 84 or embodiment 83, wherein the web 148 is arranged at a surface different from a surface at which the projection 154 is arranged.
87. The autoinjector 10 according to one or more of the preceding embodiments, further comprising a needle guard 18, wherein an axial movement of the needle guard 18 towards the drive chassis 24 releases the fixing of the drive chassis 24 with respect to the housing 12.
88. The autoinjector 10 according to embodiment 87, wherein the needle guard 18 comprises a blocking rib 144.
89. The autoinjector 10 according to embodiment 87 or embodiment 88, wherein the needle guard 18 engages the trigger arm 36 on axially moving toward the drive chassis 24.
90. The autoinjector 10 according to one of embodiments 87 to 89 and embodiment 85, wherein the needle guard 18 comprises an engagement surface 146 configured to engage the web 148 of the trigger arm 36.

91. The autoinjector 10 according to embodiment 88 or embodiment 89 and embodiment 90, wherein the engagement surface 146 projects from the rib.
92. The autoinjector 10 according to one of embodiments 80 to 86, wherein the web 148 comprises a deflection surface 150 inclined with respect to a movement direction of the drive chassis 24.
93. The autoinjector 10 according to one of embodiments 85 to 87, wherein the engagement surface 146 is inclined with respect to a movement direction of the drive chassis 24.
94. The autoinjector 10 according to embodiment 92 and embodiment 93, wherein the engagement surface 146 and the deflection surface 150 are inclined with respect to a movement direction of the drive chassis 24 in a cooperating manner.
95. The autoinjector 10 according to one of embodiments 78 to 94, wherein the drive spring 74 is configured to drive the drive chassis 24 towards the needle guard 18 after activation of the autoinjector 10.
96. The autoinjector 10 according to one or more of the preceding embodiments, wherein the drive chassis 24 further comprises a plunger support 44 for engaging a piston of the pre-filled syringe 16.
97. The autoinjector according to embodiment 96, wherein a relaxation of the drive spring 74 drives the plunger support 44 towards the plunger 26 of the pre-filled syringe 16.
98. The autoinjector according to one of the preceding embodiments, wherein the drive chassis 24 is of generally U-shaped design.
99. The autoinjector according to one or more of the preceding embodiments, wherein the trigger arm 36, the drive chassis 24 and the plunger support 44 are formed in one piece from the same material.
100. An autoinjector 10, optionally in accordance with one or more of the preceding embodiments, the autoinjector 10 comprising a pre-filled syringe 16 arranged within a housing 12 of the autoinjector 10, a needle shield 78 covering a needle 34 of the pre-filled syringe 16 in a storage state of the autoinjector 10, an axially moveable needle guard 18 arranged to cover the needle 34 of the pre-filled syringe 16 at least after use of the autoinjector 10 and to move relative to the pre-filled syringe 16 during use of the autoinjector 10, as well as a removable cap 70 in which the needle guard 18 is stored in the storage state of the autoinjector 10, wherein the cap 70 is removably connected to the needle guard 18 in the storage state of the autoinjector 10, and wherein, on removal of the cap 70, the needle shield 78 is also removed from the autoinjector 10.
101. The autoinjector according to one or more of the preceding embodiments, wherein the needle guard 18 is connected to the cap 70 via one or more snap fit connections 94.
102. The autoinjector according to embodiment 101, wherein each snap fit connection 94 comprises a snap-fit projection 96 cooperating with a corresponding snap-fit area 98.
103. The autoinjector according to embodiment 102, wherein one or more snap-fit projections 96 are provided at an outer surface 126 of the needle guard 18.
104. The autoinjector according to embodiment 101 or embodiment 102, wherein one or more snap-fit areas 98 are provided at an inner surface of the cap 70.
105. The autoinjector according to one or more of the preceding embodiments, wherein an outer wall 116 of the cap 70 contacts an outer wall 136 of the housing 12 in a storage state of the autoinjector 10.
106. The autoinjector according to embodiment 105, wherein the outer wall 116 of the cap 70 and the outer wall 136 of the housing 12 do not overlap in an axial direction of the autoinjector 10.
107. The autoinjector according to embodiment 105 or embodiment 106, wherein the outer wall 116 of the cap 70 and the outer wall 136 of the housing 12 radially overlap in the storage state of the autoinjector 10.
108. The autoinjector according to one or more of the preceding embodiments, wherein the cap 70 prevents axial movement of the needle guard 18 when attached to the needle guard 18 in the storage state.
109. The autoinjector according to one or more of the preceding embodiments, wherein the needle shield 78 is arranged within an inner wall of the cap 70 in the storage state of the autoinjector 10.
110. The autoinjector according to one or more of the preceding embodiments, wherein a front end of the needle guard 18 is arranged within an opening 124 of the cap 70.
111. The autoinjector according to one or more of the preceding embodiments, wherein a front end 122 of the needle guard 18 is arranged within an opening 124 of the cap 70 and wherein the opening 124 is formed between the outer wall 116 of the cap 70 and the inner wall of the cap 70.
112. The autoinjector according to one or more of the preceding embodiments, wherein a front end 122 of the needle guard 18 is arranged within an opening 124 of the cap 70 and wherein the front end 122 of the needle guard 18 comprises the one or more snap-fit projections 96.
113. The autoinjector according to one or more of the preceding embodiments, wherein an inner surface 128, 132 of the housing 12 comprises one or more grooves 130, 134 in which one or more of the snap-fit projections 96 can axially move relative to the housing 12 on a movement of the needle guard 18.
114. The autoinjector according to one or more of the preceding embodiments, wherein the axially moveable needle guard 18 is arranged to move relative to the housing 12 during use of the autoinjector 10.
115. The autoinjector according to one or more of the preceding embodiments, wherein the cap 70 is of single piece design.
116. The autoinjector according to one or more of the preceding embodiments, wherein the cap 70 comprises inwardly facing projections 108 at a needle guard facing end 102 that engage a syringe facing surface 110 of the needle shield 78.
117. The autoinjector according to one or more of the preceding embodiments, wherein the inner wall 106 of the cap 70 comprises two windows 112.
118. The autoinjector 10 according to embodiment 116 and embodiment 117, wherein each projection 108 is arranged at a window 112.
119. The autoinjector 10 according to one or more of the preceding embodiments, wherein recesses 114 are formed in the inner wall of the cap 70.
120. The autoinjector 10 according to one or more of the preceding embodiments, wherein an inner surface 118 of the outer wall 116 of the cap 70 comprises one or more ribs 120.

121. The autoinjector 10 according to one or more of the preceding embodiments, wherein the cap 70 comprises a stand of the autoinjector 10.

123. The autoinjector 10 according to one or more of the preceding embodiments, wherein an axial movement of the needle guard 18 in the direction of the pre-filled syringe 16 brings about an engagement of the release mechanism 40 of a plunger 26 of the pre-filled syringe 16 for dispensing a material stored in the pre-filled syringe 16.

124. An autoinjector 10, optionally according to one or more of the preceding embodiments, the autoinjector 10 comprising:
a housing 12 in which a pre-filled syringe 16 is arranged,
a drive chassis 24 mounted in the housing 12, the drive chassis 24 being biased with respect to the housing 12 and being fixed with respect to the housing 12 in a storage state of the autoinjector 10,
a status indicator window 20 arranged at the housing 12 via which the drive chassis 24 is visible from the outside, with the status indicator window 20 showing a first part 50 of the drive chassis 24 in the storage state of the autoinjector 10 and a second part 52 of the drive chassis 24 after use of the autoinjector 10, with the first and second parts 50, 52 of the drive chassis 24 being distinguishable from one another.

125. The autoinjector 10 according to embodiment 124, wherein the status indicator window 20 is formed by an elongate slot extending radially around a part of the housing 12.

126. The autoinjector 10 according to embodiment 124 or embodiment 125, wherein the first and second parts 50, 52 of the drive chassis 24 are distinguishable from one another due to a difference in colour, a printed label applied at a surface of the drive chassis 24, a text applied on the surface 49 of the drive chassis 24 and/or an icon displayed in the surface of the drive chassis 24.

127. The autoinjector 10 according to according to one or more of the preceding embodiments, further comprising a syringe window 14 via which the pre-filled syringe 16 is visible from the outside.

128. The autoinjector 10 according to embodiment 127, wherein the syringe window 14 shows a content filled in the pre-filled syringe 16 in the storage state of the autoinjector 10.

129. The autoinjector 10 according to embodiment 127 or embodiment 128, wherein the syringe window 14 shows at least one of a plunger 26 arranged within the pre-filled syringe 16 and a part of the dispensing limb 22 in the pre-filled syringe 16 after use of the autoinjector 10.

130. The autoinjector 10 according to one of embodiments 127 to 129, wherein the syringe window 14 is arranged in the housing 12.

131. The autoinjector 10 according to one of embodiments 127 to 130, wherein the syringe window 14 is of elongate shape and a length of the elongate shape extends in an axial direction of the autoinjector 10.

132. The autoinjector 10 according to one of embodiments 127 to 131, wherein the syringe window is arranged transverse to the status indicator window 20.

134. The autoinjector 10 according to one of embodiments 127 to 132, wherein the syringe window shows a different part of the drive chassis 24 in comparison with the status indicator window 20.

135. The autoinjector 10 according to one or more of the preceding embodiments, wherein the drive chassis 24 comprises a trigger arm 36 engaging an opening 138 in the housing 12 in the storage state of the autoinjector 10.

136. The autoinjector 10 according to one or more of the preceding embodiments, further comprising a needle guard 18, wherein an axial movement of the needle guard 18 towards the drive chassis 24 releases the fixing of the drive chassis 24 with respect to the housing 12.

137. The autoinjector 10 according to embodiment 136, wherein the needle guard 18 comprises a plunger arm 142.

138. The autoinjector 10 according to embodiment 136 or embodiment 137, wherein the needle guard 18 engages the trigger arm 36 on axially moving toward the drive chassis 24.

139. The autoinjector 10 according to embodiment 137 or embodiment 138, wherein the plunger arm 142 of the needle guard 18 engages the trigger arm 36 on axially moving toward the drive chassis 24.

140. The autoinjector 10 according to one or more of the preceding embodiments, further comprising a drive spring 74 mounted between an end of the housing 12 and the drive chassis 24.

141. The autoinjector 10 according to embodiment 140, wherein the spring is configured to drive the drive chassis 24 towards the needle guard 18 after activation of the autoinjector 10.

141. The autoinjector 10 according to one or more of the preceding embodiments, wherein the drive chassis 24 further comprises a plunger support 44 for engaging a piston of the pre-filled syringe 16.

142. The autoinjector 10 according to embodiment 139 or embodiment 140 and embodiment 141, wherein the relaxation of the drive spring 74 drives the plunger support 44 towards the piston of the pre-filled syringe 16.

143. The autoinjector 10 according to one or more of the preceding embodiments, wherein the drive chassis 24 is of generally U-shaped design.

144. The autoinjector 10 according to one or more of the preceding embodiments, wherein the trigger arm 36, the drive chassis 24 and the plunger support 44 are formed in one piece from the same material.

145. An autoinjector 10, optionally according to one or more of the preceding embodiments, comprising a drive chassis 24, the drive chassis 24 comprising a dispensing limb 22 and a trigger limb 32, wherein a plunger 26 is arranged at a proximal end of the dispensing limb 22 and a trigger arm 36 is arranged extending proximally from the trigger limb 32, wherein the trigger limb 32 and the dispensing limb 22 are arranged in parallel to one another respectively at least essentially in parallel to one another and are connected to one another at a respective distal side of the dispensing limb 22 and the trigger limb 32.

146. An autoinjector 10 according to embodiment 145, wherein the trigger limb 32, the dispensing limb 22, the plunger support 44 and the trigger arm 36 are integrally formed in one piece.

147. An autoinjector 10 according to embodiment 145 or embodiment 146, wherein the trigger arm 36 is biased with respect to a housing 12 of the autoinjector 10 in a storage state of the autoinjector 10.

148. The autoinjector 10 according to one or more of the preceding embodiments, wherein the trigger arm 36 is deflected upon moving the autoinjector 10 from a storage state into an activated state of the autoinjector 10.

149. The autoinjector 10 according to one or more of the preceding embodiments, wherein the trigger arm 36 is actuated on by a needle guard 18 of the autoinjector 10 upon moving the autoinjector 10 from a storage state into an activated state of the autoinjector 10.

150. The autoinjector 10 according to one or more of the preceding embodiments, wherein the plunger support 44 is configured to act on a pre-filled syringe 16 of the autoinjector 10.

151. The autoinjector 10 according to one or more of the preceding embodiments, further comprising a drive spring 74.

152. The autoinjector 10 according to embodiment 151, wherein the drive spring 74 is arranged within a housing 12 of the autoinjector 10 between a distal housing wall 84 and the drive chassis 24.

153. The autoinjector 10 according to embodiment 152, wherein the drive spring 74 biases the trigger arm 36 in a storage state of the autoinjector 10 with respect to the housing 12 of the autoinjector 10.

154. The autoinjector 10 according to one of embodiments 151 to 153, wherein the drive spring 74 is configured to drive the plunger 26 of the autoinjector 10 in a pre-filled syringe 16 of the autoinjector 10.

155. The autoinjector 10 according to one or more of the preceding embodiments, wherein the drive chassis 24 is linearly guided within a housing 12 of the autoinjector 10 upon moving the autoinjector 10 from a storage state into an activated state of the autoinjector 10.

156. The autoinjector 10 according to one or more of the preceding embodiments, wherein the trigger arm 36 is configured to move radially and transversely with respect to the trigger limb 32.

156. The autoinjector 10 according to one or more of the preceding embodiments, wherein the trigger arm 36 is configured to cooperate with a stop feature 54 arranged at the housing 12 in a storage state of the autoinjector 10.

158. The autoinjector 10 according to one or more of the preceding embodiments, wherein the trigger limb 32 and the dispensing limb 22 are arranged in an at least generally U-shaped manner respectively in a U-shaped manner.

159. The autoinjector 10 according to one or more of the preceding embodiments, wherein the trigger limb 32 further comprises at least a first part 56 of an audible end of dose feedback member 58.

160. The autoinjector 10 according to embodiment 159, further comprising a housing 12, wherein the housing 12 further comprises at least one second part 66 of the audible end of dose feedback member 58, optionally wherein the housing 12 is formed by an outer body 82 and an inner body 80 and one of the inner body 80 and the outer body 82 comprises the at least one second part 66 of the audible end of dose feedback member 58.

161. The autoinjector 10 according to embodiment 159 or embodiment 160, wherein the first and second parts 56, 66 of the audible end of dose feedback members 58 are formed by a recess 208 and a latching tongue 62 configured to cooperate with the recess 208.

162. The autoinjector 10 according to one of embodiments 159 to 161, wherein the audible end of dose feedback member 58 is configured to emit a sound once the material has been dispensed from the autoinjector 10.

163. The autoinjector 10 according to one of embodiments 159 to 162, wherein the audible end of dose feedback member 58 is configured to emit a sound between the drive chassis 24 and the housing 12 once the material has been dispensed from the autoinjector 10.

164. The autoinjector 10 according to one or more of the preceding embodiments, wherein the inner body 80 further comprises a first cut-out 174, with the first cut-out 74 being configured to cooperate with a clip arm 184 and a lock-out arm 186 of the needle guard 18.

165. The autoinjector 10 according to embodiment 164, wherein the inner body 80 further comprises a second cut-out 176, with the second cut-out being configured to cooperate with the lock-out arm 186 of the needle guard 18.

166. The autoinjector 10 according to one or more of the preceding embodiments, wherein the drive chassis 24 further comprises a second trigger arm 36.

167. The autoinjector 10 according to embodiment 166, wherein the second trigger arm 36 is arranged at a side of the drive chassis 24 disposed opposite to the first trigger arm 36.

168. The autoinjector 10 according to one or more of the preceding embodiments, wherein the trigger limb 32 comprises a passage 140 formed therein.

169. The autoinjector 10 according to embodiment 168, wherein the passage 140 is configured to receive at least a part of the drive spring 74.

170. The autoinjector 10 according to one or more of the preceding embodiments, wherein the trigger limb 32 comprises a lip 216 at an end disposed opposite to the web 42.

171. The autoinjector 10 according to embodiment 170, wherein the lip 216 is configured to engage clip arms 184 formed at the needle guard 18.

172. The autoinjector 10 according to embodiment 170 or embodiment 171, wherein the lip 216 comprises two tips 218, with each tip 218 being configured to engage a respective one of a clip arm 184 formed at the needle guard 18.

173. The autoinjector 10 according to one or more of the preceding embodiments, wherein the needle shield 78 comprises a needle receptacle 212 configured to receive the needle 34 of the pre-filled syringe 16.

174. The autoinjector 10 according to one or more of the preceding embodiments, wherein the cap 70 comprises a needle shield holder 104 that is configured to receive the needle shield 78.

175. The autoinjector 10 according to one or more of the preceding embodiments, wherein the needle guard 18 further comprises one or more lock-out arms 186.

176. The autoinjector 10 according to embodiment 175, wherein the one or more lock-out arms 186 are configured to cooperate with the inner body 80.

177. The autoinjector 10 according to embodiment 175 or embodiment 176, wherein the one or more lock-out arms 186 are configured to engage one or more bars 178 of the inner body 80 in the lock-out state.

178. The autoinjector 10 according to one of embodiments 175 to 177, wherein the one or more lock-out arms 186 are configured to engage a respective one of one or more cut-outs 176 of the inner body 80 in the lock-out state.

179. The autoinjector 10 according to one of embodiments 175 to 178, wherein the one or more lock-out arms 186 are configured to engage one or more further cut-outs 174 of the inner body 80 in the dispensing state and in the storage state.

180. The autoinjector 10 according to one or more of the preceding embodiments, wherein the needle guard 18 further comprises one or more clip arms 184.

181. The autoinjector 10 according to embodiment 180, wherein the one or more clip arms 184 are configured to cooperate with a respective one of one or more cut-outs 174 of the inner body 80 in the dispensing state.

182. The autoinjector 10 according to embodiment 180 or embodiment 181, wherein the one or more clip arms 184 are deflected inwardly and abut an inner surface 132 of the inner body 80 in the lock-out state.

183. The autoinjector 10 according to one of embodiments 180 to 182, wherein the one or more clip arms 184 are configured to be deflected inwardly by the drive chassis 24 on a proximal movement of the drive chassis 24.

184. The autoinjector 10 according to one or more of the preceding embodiments, wherein the needle guard 18 further comprises a plunger arm 142.

185. The autoinjector 10 according to embodiment 184, wherein the plunger arm 142 comprises one or more blocking ribs 144 arranged at a distal end thereof.

186. The autoinjector 10 according to embodiment 185, wherein the plunger arm 142 comprises two blocking ribs 144, with the two blocking ribs 144 being arranged oppositely disposed to one another.

187. The autoinjector 10 according to embodiment 185 or embodiment 186, wherein the one or more blocking ribs 144 are configured to block a radial movement of the trigger arm 36 in the storage state.

188. The autoinjector 10 according to one of embodiments 184 to 187, wherein the plunger arm 142 comprises one or more cams 162.

189. The autoinjector 10 according to embodiment 188, wherein the one or more cams 162 are configured to engage the one or more trigger arms 36 of the drive chassis 24 on activation of the autoinjector 10.

190. The autoinjector 10 according to embodiment 189, wherein the one or more cams 162 are configured to entrain the one or more trigger arms 36 of the drive chassis 24 in the transverse direction T upon activation of the autoinjector 10.

191. The autoinjector 10 according to one or more of the preceding embodiments, wherein the needle guard 18 comprises one or more protrusions 166 cooperating with a respective one of one or more elongate holes 168 present in the inner body 80.

192. The autoinjector 10 according to embodiment 191, wherein the one or more protrusions 166 are provided to ensure a linear guidance of the needle guard 18 relative to the inner body 80.

193. The autoinjector 10 according to one or more of the preceding embodiments, wherein the needle guard 18 further comprises one or more anti-pull off features 170.

194. The autoinjector 10 according to embodiment 193, wherein the one or more anti-pull off features 170 are configured to prevent a removal of the needle guard 18 from the proximal end of the housing 12.

195. The autoinjector 10 according to embodiment 194, wherein the inner body 80 comprises one or more elongate holes 168 each having a proximal stop 172, wherein the proximal stop 172 prevents a respective one of the protrusions 166 from being moved proximally beyond the stop 172.

196. The autoinjector 10 according to one or more of the preceding embodiments, wherein the inner body 80 of the housing 12 further comprises at least a part 66 of an audible end of dose feedback member 58.

197. The autoinjector 10 according to embodiment 196, wherein the part 66 of the audible end of dose feedback member 58 comprises an inner body recess 206 having a distal surface 196 and a proximal surface 198 surrounding the inner body recess 206.

198. The autoinjector 10 according to one or more of the preceding embodiments, wherein the inner body 80 comprises one or more cut-outs 174, 176.

199. The autoinjector 10 according to embodiment 198 and embodiment 196 or 197, wherein the one or more cut-outs 174, 176 are arranged at an end of the inner body 80 disposed opposite to the second part 66 of the audible end of dose feedback member 58.

200. The autoinjector 10 according to one or more of the preceding embodiments, wherein the outer body 82 comprises one or more stop features 54.

201. The autoinjector 10 according to embodiment 200, wherein each stop feature 54 is provided at a respective opening 138.

202. The autoinjector 10 according to embodiment 200 or embodiment 201, wherein the respective stop feature 54 is a component of a respective release mechanism 40 of the autoinjector 10.

203. The autoinjector 10 according to one or more of the preceding embodiments, wherein an outer surface 49 of the trigger limb 32 comprises a first and a second part outer surface 50, 52 whose appearance differ from one another.

204. A method of activating an autoinjector 10, optionally according to one or more of the preceding embodiments, the method comprising the steps of:
  releasing a snap-fit connection 94 between a cap 70 and a needle guard 18;
  axially moving the cap 70 away from the needle guard 18; and thereby simultaneously removing a needle shield 78 from a pre-filled syringe 16.

205. A method of assembling an autoinjector 10, optionally according to one or more of the preceding embodiments, the method comprising the steps of:
  providing a pre-filled syringe 16,
  providing a needle shield 78,
  covering a needle 34 of the pre-filled syringe 16 with the needle shield 78; and
  inserting the needle shield 78 and needle 34 into a cap 70.

What is claimed is:

1. An autoinjector comprising:
  a proximal end;
  a distal end, the autoinjector extending along an axial direction from the proximal end to the distal end;
  a housing;
  a drive chassis arranged linearly moveable within the housing, the drive chassis comprising a dispensing limb and a trigger limb extending along the axial direction;
  a plunger arranged at the proximal end of the dispensing limb; and
  a trigger arm arranged extending proximally from the trigger limb, the trigger limb and the dispensing limb arranged essentially in parallel to one another-, the trigger limb being disposed in a transverse direction to the dispensing limb, the transverse direction being orthogonal to the axial direction, and the trigger limb and the dispensing limb being connected to one another at a respective distal end of the dispensing limb and the trigger limb, the trigger arm configured to move in a radial direction and the transverse direction with respect to the trigger limb, the radial direction being orthogonal to both the transverse direction and the axial direction.

2. The autoinjector according to claim 1, wherein the trigger limb, the dispensing limb, and the trigger arm are integrally formed in one piece.

3. The autoinjector according to claim 1, wherein the trigger arm is biased with respect to the housing in a storage state of the autoinjector.

4. The autoinjector according to claim 1, wherein the trigger arm is configured to be deflected relative to the housing upon moving the autoinjector from a storage state into a dispensing state.

5. The autoinjector according to claim 1, further comprising a needle guard, and the trigger arm is actuated on by the needle guard upon moving the autoinjector from a storage state into a dispensing state.

6. The autoinjector according to claim 1, wherein an outer surface of the trigger limb comprises a first part outer surface and a second part outer surface with differing appearances.

7. The autoinjector according to claim 1, further comprising a drive spring arranged within the housing between a distal housing wall and the drive chassis.

8. The autoinjector according to claim 7, wherein the drive spring is configured to bias the trigger arm in a storage state of the autoinjector with respect to the housing.

9. The autoinjector according to claim 7, wherein the trigger limb is configured to receive at least a part of the drive spring.

10. The autoinjector according to claim 7, wherein the drive spring is configured to drive the plunger into a pre-filled syringe of the autoinjector.

11. The autoinjector according to claim 1, wherein the drive chassis is linearly guided within the housing upon moving the autoinjector from a storage state into a dispensing state.

12. The autoinjector according to claim 1, wherein the trigger arm is configured to cooperate with a stop feature arranged at the housing in a storage state of the autoinjector.

13. The autoinjector according to claim 1, wherein the trigger limb and the dispensing limb are arranged in an at least generally U-shaped manner.

14. The autoinjector according to claim 1, wherein the trigger limb further comprises at least a first part of an audible end of a dose feedback member, or the audible end of the dose feedback member is configured to emit a sound once material has been dispensed from the autoinjector, or the audible end of the dose feedback member is configured to emit a sound between the drive chassis and the housing once the material has been dispensed from the autoinjector.

15. The autoinjector according to claim 1, wherein the trigger limb further comprises at least a first part of an audible end of a dose feedback member and the housing comprises at least a second part of the audible end of the dose feedback member, and the first and second parts of the audible end of the dose feedback member are formed by a recess and a latching tongue configured to engage the recess, or the audible end of dose feedback member is configured to emit a sound once material has been dispensed from the autoinjector, or the audible end of the dose feedback member is configured to emit a sound between the drive chassis and the housing once the material has been dispensed from the autoinjector.

\* \* \* \* \*